United States Patent
Ueno et al.

(10) Patent No.: US 6,409,812 B1
(45) Date of Patent: Jun. 25, 2002

(54) AZO COMPOUNDS AND PROCESS FOR PRODUCING THE SAME

(75) Inventors: Ryuzo Ueno, Nishinomiya; Masaya Kitayama, Takarazuka; Kenji Minami, Sennan; Hiroyuki Wakamori, Hyogo-ken, all of (JP)

(73) Assignee: Kabushiki Kaisha Ueno Seiyaku Oyo Kenkyujo, Osaka (JP)

(*) Notice: Subject to any disclaimer, the term of this patent is extended or adjusted under 35 U.S.C. 154(b) by 0 days.

(21) Appl. No.: 09/581,704

(22) PCT Filed: Oct. 14, 1999

(86) PCT No.: PCT/JP99/05656

§ 371 (c)(1),
(2), (4) Date: Jun. 16, 2000

(87) PCT Pub. No.: WO00/23525

PCT Pub. Date: Apr. 27, 2000

(30) Foreign Application Priority Data

Oct. 16, 1998 (JP) .............................. 10/295215
Apr. 13, 1999 (JP) .............................. 11/105206
Jun. 23, 1999 (JP) .............................. 11/176626

(51) Int. Cl.$^7$ .................. C09D 11/00; C09B 29/20; C07C 69/76

(52) U.S. Cl. ................ 106/31.51; 106/31.48; 106/31.5; 106/31.77; 106/31.79; 106/31.8; 106/496; 106/534; 106/799; 106/841; 106/860; 106/866; 106/560; 106/100

(58) Field of Search ............ 106/31.51, 31.5, 106/31.48, 31.77, 31.79, 31.8, 496; 534/799, 841, 860, 866; 560/100; 430/72

(56) References Cited

U.S. PATENT DOCUMENTS 3,821,191 A * 6/1974 Ruider et al. ............ 106/31.78
3,877,957 A * 4/1975 Bradley et al. .......... 106/31.78
4,115,055 A * 9/1978 Kirner et al. ............... 534/863
4,737,581 A * 4/1988 Hari .......................... 106/31.8
5,591,257 A * 1/1997 Weide et al. ............. 106/31.77
5,965,715 A * 10/1999 Ueno et al. .............. 106/31.81
5,973,126 A * 10/1999 Ueno et al. .............. 106/31.77
6,020,470 A * 2/2000 Ueno et al. ................. 534/635

FOREIGN PATENT DOCUMENTS

JP    10-279823    10/1998
WO    98/16587    4/1998
WO    98/17728    4/1998
WO    99/11717    3/1999

* cited by examiner

*Primary Examiner*—Helene Klemanski
(74) *Attorney, Agent, or Firm*—Sughrue Mion, PLLC

(57) ABSTRACT

A diamide type azo compound represented by the general formula (I):

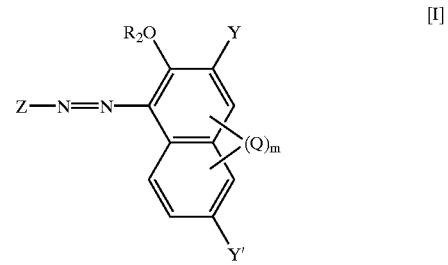

which is derived from 2-hydroxy-3,6-dicarboxylic acid and at least one of the amide moieties in the compound is an aliphatic amide moiety, various use of the same and process for preparing the same are provided.

15 Claims, 6 Drawing Sheets

AZO COMPOUNDS AND PROCESS FOR PRODUCING THE SAME

TECHNICAL FIELD

The present invention relates to a novel azo compound, a process for producing the same and use of the same. The present invention also relates to a novel naphthol derivative, which can be a starting material for synthesis of the novel azo compound of the present invention.

BACKGROUND ART

In order to provide or improve paints, inks, photosensitive materials and the like with added value or higher properties, especially to provide those with light resistance, solvent resistance, water resistance and chemical resistance, development of novel pigment or dyes have been intensively conducted. For example, the inventors had already disclosed an azo compound synthesized by using 2-hydroxynaphthalene-3,6-dicarboxylic acid, or its ester, amide or ureido derivative as a coupler(WO98/16587).

SUMMARY OF INVENTION

The present invention provides an azo compound, which exhibits outstanding water resistance, chemical resistance, thermal resistance, and especially light resistance, good dispersion property and coloring power and can provide wide range of bright color from orange to purple with excellent transparency.

The present invention provides a novel azo type coloring agent obtained by modifying 3- and/or 6-carboxy group of 2-hydroxynaphthalene-3,6-dicarboxylic acid with an alkylamide derivative. The azo compound of the present invention exhibits an excellent light resistance.

Accordingly, the present invention relates to a novel azo compound having the general formula (I):

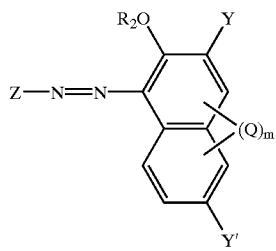

[I]

wherein Y is —(CONH)n-X or an optionally esterified carboxyl group,

Y' is —(CONH)n-X' or an optionally esterified carboxyl group, (wherein X and X' are optionally substituted and/or branched saturated or unsaturated aliphatic hydrocarbon groups, optionally substituted aromatic groups, or optionally substituted heterocyclic groups having conjugated double bonds, n is an integer of 1 or 2, provided that when either Y or Y' is a carboxylic group, said carboxylic group may optionally form an acceptable salt), $R_2$ is a hydrogen atom, an optionally branched alkyl group having 1–6 carbon atoms, an acyl group having 1–6 carbon atoms or a phenyl alkyl group, Q is an optionally branched alkyl group having 1–6 carbon atoms, an optionally branched alkoxy group having 1–6 carbon atoms, a halogen atom, a sulfo group, a nitro group, a nitroso group, or an amino group, m is an integer of 0–3, provided that when m is 1, the Q may be combined with either of the two condensed rings, when m is 2 or 3, the Qs may be combined with either or both of the condensed rings, or may form a ring together with the two condensed rings, Z is an optionally substituted monovalent aromatic group, and provided that at least one of Y and Y' represents a group wherein X or X' is an optionally substituted and/or branched unsaturated or saturated aliphatic hydrocarbon group;

a process for producing the same, and coloring composition comprising the azo compound of the present invention. According to the present application, the term "coloring composition" include pigment, ink, paint, dye, masscoloring agent for polymer material and charge generating material, and the like.

The present invention also provides a novel naphthol derivative having the general formula (IV):

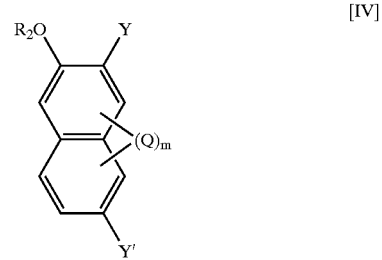

[IV]

wherein Y is —(CONH)n-X or an optionally esterified carboxyl group,

Y' is —(CONH)n-X' or an optionally esterified carboxyl group, (wherein X and X' are optionally substituted and/or branched saturated or unsaturated aliphatic hydrocarbon groups, optionally substituted aromatic groups, or optionally substituted heterocyclic groups having conjugated double bonds, n is an integer of 1 or 2, provided that when either Y or Y' is a carboxylic group, said carboxylic group may optionally form an acceptable salt), $R_2$ is a hydrogen atom, an optionally branched alkyl group having 1–6 carbon atoms, an acyl group having 1–6 carbon atoms or a phenyl alkyl group, Q is an optionally branched alkyl group having 1–6 carbon atoms, an optionally branched alkoxy group having 1–6 carbon atoms, a halogen atom, a sulfo group, a nitro group, a nitroso group, or an amino group, m is an integer of 0–3, provided that when m is 1, the Q may be combined with either of the two condensed rings, when m is 2 or 3, the Qs may be combined with either or both of the condensed rings, or may form a ring together with the two condensed rings, and provided that at least one of Y and Y' represents a group wherein X or X' is an optionally substituted and/or branched unsaturated or saturated aliphatic hydrocarbon group.

As described above, the coupler used in this invention, i.e. the compound represented by the general formula [IV], may be synthesized from 2-hydroxynaphthalene-3,6-dicarboxyamide, or ureide or carboxylic acid derivative thereof. The starting material, 2-hydroxynaphthalene-3,6-dicarboxylic acid may be obtained by means of Kolbe-Schmitt reaction, i.e. by reacting potassium 2-hydroxynaphthalene with carbon dioxide in the presence of a potassium salt such as potassium phenoxide under high pressure and high temperature.

In the present invention, the amide or ureide derivative may be prepared by obtaining acid chloride of the starting compound by means of thionyl chloride or the like in a solvent such as xylene or sulfolane in a conventional manner, and then reacting the acid chloride with amine or urea. Alternatively, they can be prepared by reacting the starting compound directly with amine or urea in the presence of phosphorous trichloride, dicyclohexylcarbodiimide or the like.

Examples of the amines or ureas, starting materials which constitutes the group X or X' in the Y or Y' may include optionally substituted and/or branched saturated or unsaturated aliphatic amines, optionally substituted aromatic amino compounds such as aniline (X or X' is a phenyl group), amino naphthalene (X or X' is a naphthyl group), aminoanthracene (X or X' is a anthryl group), aminopyrene (X or X' is a pyrenyl group), amino fluorene (X or X' is a fluororenyl group) or aminoanthraquinone (X or X' is an anthraquinonyl group); and optionally substituted heterocyclic compounds having conjugated double bond(s) such as aminobenzimidazolone (X or X' is a benzimidazolonyl group), aminocarbazole (X or X' is a carbazolyl group), aminopyridine (X or X' is a pyridyl group), aminothiazole (X or X' is a thiazolyl group), aminobenzothiazole (X or X' is a benzothiazolyl group), or aminoimidazole (X or X' is an imidazolyl group) as well as aminoindole (X or X' is an indolyl group), aminothiophene (X or X' is a thiofuryl group), aminophenothiazine (X or X' is a phenothiazinyl group), aminoacridine (X or X' is an acridinyl group), and aminoquinoline (X or X' is a quinolinyl group). Examples of the substituents include halogen atoms, nitro group, lower alkyl groups, lower alkoxy groups, cyano groups, phenyl groups, morpholino groups, phenoxy groups, sulfo groups, carboxyl groups, amide groups (for example, phenylaminocarbonyl group) and the like, and the phenoxy and amide groups may also have another substituent such as halogen atom, lower alkyl group, lower alkoxy group, alkylaminosulfonyl group, nitrile group or the like.

In the present invention, at least one of Y and Y' in the compound of the formulae [I] and [IV] represents a group wherein X or X' is an optionally substituted and/or branched saturated or unsaturated aliphatic hydrocarbon group.

Ureas may be prepared by reacting the above-described amino compound with potassium cyanate. That is, for example, phenylurea may be obtained from aniline. Y or Y' may represent an optionally esterified carboxyl group, for example those represent by the general formula of —COR or —COR'. When either R or R' is a hydroxy group, it may form an acceptable salt. The term "an acceptable salt" represents a salt, which does not impair diazotizing reaction and does not have any adverse effect on the coloring and light resistance properties of the compound. Examples of the salts include alkaline metal salts and alkaline earth metal salts, and alkaline metal salts are preferable. Examples of the alkaline metals include sodium, potassium, lithium and the like. When Y or Y' is an optionally esterified carboxyl group, R or R' may be an optionally branched alkoxy group having 1–6, preferably 1–4 carbon atoms, a phenyloxy group, a benzyloxy group, or a phenacyloxy group, each of the groups may be substituted. $R_2$ is a hydrogen atom, an optionally branched alkyl group having 1–6, preferably 1–4 carbon atoms, especially, methyl or ethyl group; an acyl group having 1–6, preferably 1–4 carbon atoms, especially acetyl group; or a phenylalkyl group wherein the phenyl moiety may have a substituent such as a halogen atom or a lower alkyl group.

As described above, one of the essential features of the present invention is that at least one of X and X' is an optionally substituted and/or branched saturated or unsaturated aliphatic hydrocarbon group. Said aliphatic hydrocarbon group preferably has 1–30, more preferably 1–20 carbon atoms. The aliphatic hydrocarbon group may be a straight or branched chain, or may form a ring, and preferably, be a straight chain. The group may optionally have an unsaturated bond or a substituent. Examples of the substituents include cycloaliphatic groups, such as cyclopentyl and cyclohexyl groups, aromatic groups, such as phenyl and naphthyl groups, heterocyclic groups such as furyl, piperidyl, pyridyl, morpholino, thiofuryl, indolyle, carbazolyle groups and the like, halogen atoms such as fluorine, chlorine, bromine, iodine and the like, alkoxy groups, cycloalkylamino groups, alkylamino groups, nitro group, hydroxy group, and carboxyl groups and the like. When X or X' has a hydrocarbon substituent such as a cycloaliphatic or an aromatic group, the number of the carbon atoms defined above represents those of the alkyl moiety. When the alkyl moiety has a branch, the above defined carbon number includes the carbon atoms of the branch. Examples of the optionally substituted alkyl groups include methyl, ethyl, propyl, isopropyl, butyl, isobutyl, tert-butyl, ethylhexyl, pentyl, hexyl, octyl, dimethylhexyl, octyl, dodecyl, hexadecyl, octadecyl, eicosyl, triacontyl, octadecenyl, benzyl, phenylethyl, phenylbutyl, cyclohexylaminopropyl, morphorino propyl, pyridyl methyl, furfuryl, trimethoxysilylpropyl amino ethyl, and triethoxysilyipropyl. They may have another substituent, for example, a halogen atom, a lower alkyl group, a lower alkoxy group, nitro group and amino group.

According to the present invention, the most preferable azo compound is that of the formula wherein X (i.e. the substituent at the position 3 of the formula IV) is an aromatic group, especially a naphthyl group, and X' (at the position 6 of the formula IV) is a saturated or unsaturated aliphatic hydrocarbon group which may optionally have a substituent and/or a branch.

Examples of the aromatic amines which react with the naphthol derivative of formula IV to give Z group include aniline, monoamino condensed polycyclic hydrocarbons such as naphthylamine, monoaminoanthracene, monoaminoindene, monoaminofluorenone, monoamino indole, monoaminobenzothiophene, monoaminoquinoline, and monoaminocarbazole. The above-described aromatic amines may have a substituent. Examples of the substituents include halogen atoms, lower alkyl groups, especially methyl, halogenated lower alkyl groups, cyano group, nitro group, lower alkoxy groups, amide groups, sulfo groups, alkylamino sulfonyl groups, aminocarbonyl groups, phenylaminocarbonyl groups, phenoxy groups, alkoxycarbonyl groups, hydroxy group, benzoylamino group, toluidinylamino group, triazinylamino group, pyrimidinylamino group, sulfato lower alkylsulfonyl groups, sulfato lower alkylcarbonyl groups, sulfato lower alkylsulfonyl amino groups and sulfato lower alkylcarbonyl amino groups. When the substituent comprises an aromatic or a heterocyclic group, said group may have further substituent. Examples of the further substituent may include halogen atoms, lower alkyl groups, and naphthyl amino and phenyl amino groups which may have further substituent such as sulfo group or sulfato loweralkylsulfonyl group.

The aromatic amine, which constitutes the group Z may preferably be aniline or naphthylamine.

The azo compound of the present invention can be obtained by coupling a diazonium compound, which can be obtained by diazotizing of an aromatic compound by means of sodium nitrite or the like, with a naphthol compound of formula (IV). This coupling reaction procedure is not limited and may be conducted under any conventional condition employed in a conventional method for synthesizing an azo compound. Generally, the reaction may be conducted at about 0–100° C. for about 1–24 hours.

The azo pigment obtained by the present invention may be used for preparing a lake pigment. Agents which is used to make the lake pigment may include Ca salt, Ba salt, Sr salt and Mn salt. The lake pigment may be prepared in a conventional manner.

The azo compound of the present invention may be those synthesized by means of a mixed coupler composition comprising a certain coupler of the present invention and one or more couplers selected from any other couplers including those of the present invention.

The azo compound of the present invention may be applied for pigment, ink, paint, dye, and mass coloring agent for polymer material.

For preparing a pigment with good dispersibility, the azo compound of the present invention can be milled in a solvent such as toluene, xylene, ethanol, n-butanol, iso butanol, benzylalcohol, butyl cellosolve, ethyl acetate, mineral terpene or petroleum naphtha, by means of ball mill or the like. At the milling of the azo compound, a dispersing agent may be admixed. Examples of the dispersing agents include aliphatic polyvalent carboxylic acids, amine salt of a high molecular weight polyester, polyether/ester type surfactants, long chain amine salt of a high molecular weight polycarboxylic acid, amideamine salt of a high molecular weight polyester acid, salt of a long chain polyaminoamide and a higher acid polyester, salt of a long chain polyamino amide and phosphoric acid, polyamide surfactants and phosphate surfactants.

According to the present invention, an ink composition may be prepared by dispersing the azo compound of the present invention into a vehicle, such as varnish, by means of a beads mill or a triple roll mill, and admixing an auxiliary agent therewith. By choosing a suitable vehicle based on the manner of printing, purpose, drying manner, printing material, and the like, a variety of inks, such as inks for offset printing, for photogravure, water-base ink and UV resistance ink, can be obtained. Examples for vehicle may include rosin-modified phenol resin, rosin-ester resin, petroleum resin, alkyd resin, calcium rhodinate, polyamide resin, nitro cellulose, acrylic resin, polyurethane resin, vinyl chloride, rubber resin, styrene maleate resin, polyol resin, epoxy resin, and urethane-acrylate resin. The ingredients as above may be admixed with a solvent or a diluent, and knead to provide a desired ink composition. Examples of the solvent or diluent may include vegetable oils, petroleum hydrocarbon solvents, aromatic hydrocarbons, alcohols, ketones, aromatic esters, water, and photopolymerizable acrylate monomers. Examples of the auxiliary agent include a dry controlling agent, a viscosity controlling agent, a dispersing agent, a color controlling agent, and reacting agent, as well as a defoaming agent.

According to the present invention, an well dispersed paint composition with a good dispersibility may be prepared by milling the azo composition of the present invention together with a thermosetting resin, such as melamine resin, alkyd resin, and epoxy resin in a volatile solvent, such as xylene. The paint composition may be applied on the surface of a steel board and then baked to provide coatings with good gloss. In the milling process, following additives may be added to the mixture. Examples of the additives include polymerized vegetable-oils, polyether/ester surfactants, phosphate ester surfactants, sulfate ester/anionic surfactants, hydrogenated castor oils, amides, fatty acid amide waxes, aliphatic polyvalent carboxylic acids, long chain amine salt of a high molecular weight polycarboxylic acid, salt of a long chain polyaminoamide and a higher acid polyester, salt of a long chain polyaminoamide and phosphoric acid, amine salt of polyester, and polyethylene oxides.

The azo compound of the present invention exhibits a superior dispersing and coloring quality and also good transparency, which is an essential property required for metallic coating. Therefore, the compound of the present invention may preferably be applied for paint for car or buildings.

According to the present invention, a reactive dye composition can be obtained by treating the azo compound of the present invention having a functional group such as ethyl sulfone sulfate group in its structure in an alkaline solution to provide vinyl sulfone group. Thus obtained reactive dye can react with the hydroxy group of the fiber to be dyed and add to the group. Examples of fibers to be dyed with the reaction dye may include cellulose fibers such as cotton, linen, rayon and bemberg.

As a mass-coloring agent for a polymer material, the azo compound of the present invention can be admixed with crushed polymer material by means of an extrude kneader or the like to provide a colored molten gel. The colored polymer material may be shaped in an appropriate manner. Examples of the polymer material may include thermoplastic resins such as soft and hard vinyl chloride resin, vinylidene chloride resin, low- and high-density polyethylenes, ethylene-vinylacetate copolymer, polypropylene, polybuten, moldable and foaming polystyrene, acrylonitrile-styrene copolymer, acrylonitrile-butadiene-styrene copolymer, petroleum resin, methacrylic resin, polyvinyl alcohol, polyamide resin, fuloride resin, polycarbonate, polyacetal, polyethylen terephthalate, polybutylene terephthalate, modified polyphenylene ether, and thermosetting resins such as phenol resin, urea resin, melamine resin, unsaturated polyester resin, alkyd resin, epoxy resin, silicone resin, and urethane foam. The polymer materials may also include synthesized gum and natural gum.

The pigment comprising the azo compound of the present invention may be used as a coloring agent for ink composition for ink-jet printing systems, especially for magenta ink for full-color printing systems. In order to prepare ink for ink-jet printing, the pigment of the present invention may be dispersed in a liquid medium. Suitable liquid medium is a mixture of water and a water-soluble organic solvent. Examples of said water-soluble organic solvent include alcohols such as methanol, ethanol, propanol, butanol, isobutanol, sec-butanol, tert-butanol, pentanol, hexanol, cyclohexanol, and benzyl alcohol, polyalcohols such as ethylene glycol, diethylene glycol, triethylene glycol, polyethylene glycol, propylene glycol, dipropylene glycol, polypropylene glycol, butylene glycol, hexanediol, pentanediol, glycerin, hexanetriol and thiodiglycole, polyalchol ethers such as ethylene glycol monomethyl eter, ethylene glycol monoethyl ether, ethylene glycol monobutyl ether, diethylene glycol monoethyl ether, diethylene glycol monobutyl ether, propylene glycol monomethyl ether, propylene glycol monobutyl ether, ethylene glycol mono methyl ether acetate, triethylene glycol mono methyl ether, triethylene glycol monoethyl ether, triethylene glycol monobutyl ether, ethylene glycol monophenyl ether and propylene glycol monophenyl ether, amides such as formamide, N,N-dimethyl formamide and N,N-dimethyl acetoamide, sulfoxydes such as dimethylsulfoxides, sulfons such as sulfolane, acetonitrile, and acetone.

To provide an appropriate aqueous solution, the proportion of the organic solvent to water may preferably be less than 30 weight %, preferably about 5–20 weight %.

The pigment comprising the azo compound of the present invention may be used together with other pigments or water insoluble dyes such as oil-soluble dyes and dispersion dyes. By combined use of the pigment and the water-insoluble dye, higher image density than those obtained by respective use can be obtained.

The amount of the pigment in the ink composition is not limited but preferably about 1–15%, especially about 3–10% by weight of the whole weight of the ink composition. When the content of the pigment is less than 1% by weight, the coloring power of the ink could be poor to give printed image with insufficient image density. On the contrary, when the amount of the pigment is more than 15% by weight, it would be difficult to disperse the pigment in the ink composition uniformly.

Further, an oil-soluble dye is used with the pigment, the amount of the dye is preferably 5–50 parts by weight per 100 parts by weight of the pigment.

The ink composition of the present invention comprising the above described ingredients can be obtained in a conventional manner. Namely, the pigment may be added to an aqueous solution of the dispersing agent, the mixture may be dispersed with a dispersing means such as ball mill, and then, the dispersed mixture may be subjected to centrifugation, if desired. Then the dispersed mixture may be added with additives and the like and diluted with an aqueous medium to provide a given concentration. A small amount of ink may be prepared by adding the given amounts of aqueous medium and the additives to the dispersing system, rather than preparing the same in the above sequential manner.

The preferable viscosity of the flying ink particles is less than 40 cps, more preferably, less than 30 cps. The preferable surface tension of the frying ink particles is higher than 20 dyn/cm, more preferably, 25–80 dyn/cm.

The ink for ink-jet printing of the present invention may further comprise a viscosity modifier, a surface tension modifier, a specific resistance modifier, a film-forming material, a dispersing agent, a surfactant, a UV absorbent, an antioxidant, a pH modifier, a fading resistant agent, an anti-grime agent, and an anticorrosive agent for the purpose of improving discharging stability, compatibility with the printer head or the ink cartridge, preservation stability, image stability, and other properties.

The ink-jet printing ink of the present invention may be applied to any of conventional image recording system. When used in a electrostatic printing system, the ink preferably comprises a electronic conductivity controlling agent. The electronic conductivity controlling agent is exemplified by potassium iodide, ammonium thiocyanate, sodium thiocyanate, potassium thiocyanate, lithium nitrate and lithium chloride, and the agent may preferably be contained in the ink composition at the amount of 0.1–2.0% by weight of the composition.

Since the pigment of the present invention exhibits excellent dispersion and coloring properties, and also an excellent transparency, which is an essential feature for reproducing a full color image, the ink for ink-jet printing comprising the same as a coloring agent will provide a brilliant image.

The pigment comprising the azo compound of the present invention may be applied as a coloring agent for toners used in an electrophotographic system such as an electrostatic copier, a laser beam printer, especially for a magenta toner used in a full color printing system.

In general, toners are prepared by dispersing additives such as coloring agent in a fixing resin. Examples of the fixing resins include olefinic polymers such as styrene polymers, acrylic polymers, styrene-acrylic polymers, chlorinated polystyrene, polypropylene and ionomers, polyvinyl chloride resin, polyester resin, polyamide resin, polyurethane resins, epoxy resins, diallylphthalate resins, silicone resins, ketone resins, polyvinyl butyral resins, phenolic resins, rosin modified phenolic resins, xylene resins, rosin modified maleate resins, and rosin ester, and especially, styrene-acrylic polymers and polyester resins are preferable.

As to the coloring agent, the pigment of the present invention may be preferably used and other pigments may be added to control the color. Examples of the other pigments which may be used in combination with the pigment of the present invention include phthalocyanine, azo, anthraquinone, perinone-perylene, indigo-thioindigo, dioxazine, quinacridone, isoindoline, aniline black, and carbon black pigments.

The amount of the pigment may preferably be 1–20 parts by weight, more preferably 2–10 parts by weight per 100 parts by weight of the fixing resin. The representative additives for the toners other than colorant include charge control agent and offset preventive agent. The charge control agents are admixed to control the tribo-electricity, and there are two types of the agents based on the electricity of the toner, positive charge control agents and negative charge control agents.

Examples of the positive charge control agents include an organic compound having a basic nitric atom, for example basic dyes, amino-pyrine or pyrimidine compounds, polynuclear polyamino compounds, and amino silanes. Examples of the negative charge control agents include azo dyes containing metal, metal naphthenate dyes, metal alkylsalicylates, fatty acid soaps and resin acid soaps.

The amount of the charge controlling agent may preferably be 0.1–10 parts by weight, especially 0.5–8 parts by weight per 100 parts by weight of the fixing resin.

The offset preventive agents are added to prevent the offset appearance of the toner at the fixation process. Examples of the agents include aliphatic hydrocarbons, metal aliphatic salts, higher fatty acids, fatty acid esters and their partial saponified compounds, silicone oils, and various waxes. Especially, aliphatic hydrocarbons having about 1000–10000 weight-average molecular weight are preferable. Embodiments may include low molecular weight polypropylenes, low molecular weight polyethylenes, paraffin wax, low molecular weight olefin polymers consisting of olefin units with having 4 or more carbon atoms, silicone oil, and a mixture thereof.

The amount of the offset preventive agents is preferably 0.1 to 100 parts by weight, especially 0.5–8 parts by weight per 100 parts by weight of the fixing resin. The toners of the present invention for electrophotographic system may be used for two-component developing system together with a various known carriers. The ratio of the toner and the carrier may be the same as a conventional developing system. The developing system may be added with a fluidizing agent such as fine particles of hydrophobic silica or alumina. Further, the toner of the present invention may be a magnetic toner for one-component developing system, and said magnetic toner may be added with magnetic fine particles. Typical magnetic materials include magnesium, ferrous oxides such as hematite and ferrite, metals such as iron, cobalt, nickel, and alloys or mixtures of said metals and aluminum, cobalt, copper, lead, magnesium, tin, zinc, antimony, beryllium, bismuth, cadmium, calcium, manganese, selenium, titanium, tungsten, and vanadium.

The amount of the magnetic particles is preferably 20–300 parts by weight, especially, 50–150 parts by weight per 100 parts by weight of the fixing resin. The toner of the invention may also be prepared in a form suitable for pressure-fixing printing process and said toner may be added, if desired, with plasticizing components such as a plasticizing agent, an oil, a low melting point wax, a petroleum resin, a liquid oligomer resin, and the like.

The particle size of the toner is not limited and preferably 3–35 $\mu$m, especially, 5–20 $\mu$m.

The toner of the present invention for electrophotographic system may also be obtained by prekneading the above described ingredients by means of dry blender, Henschel mixer, ball mill or the like to provide an uniform mixture. Then the mixture may be molten and kneaded by means of a kneader such as Banbury mixer, roll, uniaxial or biaxial extrusion kneader. The kneaded mixture may be cooled and milled and, if desired, classified to give toner. Alternatively, the toner of the present invention can be prepared by a known process such as polymerizing method, microcapsule polymerization and spray-dry method.

The toner of the present invention may be prepared as a liquid toner by dispersing a coloring composition consisting of the coloring agent and a resin, in a solvent. The solvent may be those having excellent insulating properties (more than $10^{10}$ $\Omega$cm of electrical resistance) and low dielectric constant (less than 3), for example, a petroleum aliphatic hydrocarbon, n-hexane, ligroine, n-heptane, isododecane and isooctane, and halogen derivatives thereof such as carbon tetrachloride, perchloroethylene. These respective solvent may be used by itself or in combination of two or more.

The toner containing the pigment of the present invention as a colorant can provide a printing image with a high image density, an excellent color reproducibility, and a good transparency, and therefore, the toner is useful as a magenta toner for full-color printing to provide a clear image.

The pigment containing the azo compound of the present invention may also be used as a red pigment for a color filter to provide a color filter having an excellent optical property, which is used in a devise with liquid-crystal display or the like.

Said color filter may be prepared by patterning of a polymer resin composition in which the pigment is dispersed to give the primary color element, or by depositing the pigment and the polymer resin dispersed in a solvent on a patterned transparent electrode.

In this embodiment, the organic polymer resin used for the color filter is required being water-clear, and excellent in thermal and light resistance. Examples of the resins include epoxy resin, melamine resin, acrylic resin, polyimide resin and its precursor polyamic acid resin, polyester resin, unsaturated polyester resin, polycarbonate resin, photosensitive monomers and oligomers having (meth)acryloyl group, and the like. Preferably, the organic polymer is a photopolymerizable compound which has at least one ethylenic unsaturated double bond in its structure. In the color filter prepared by means of the pigment containing the azo compound of the present invention, the pigment may be admixed with some other pigments. Examples of the pigment which may be used in combination with those of the present invention include perylene pigments, quinacridone pigments, anthraquinone pigments, bisazo pigments, pyrrolopyrrole pigments, isoindolinone pigments, phthalocyanine pigments, halogenated phthalocyanine pigments and dioxadine pigments.

For preparing a color filter, the amount of the pigment may be 10–50 parts by weight per 100 parts by weight of the polymer resin.

The color filter may be prepared by a conventional method such as photolithographic method with internally added pigment, electrodepositing method, electric field micelle method or printing method. For example, according to the photolithographic method, a resin composition comprising the pigment of the present invention, photosensitive resin, photopolymerization initiator, solvent and the other ingredients may be prepared and if desired, the composition may be subjected to sonication or dispersion, and then, filtered. The obtained composition may be applied on a substrate, such as a glass plate, by means of a coating device such as spinner, and dried, irradiated via photomask with light, such as supervoltage mercury lamp, and then, developed to give one primary color element(red). Usually, the procedure as above is repeated three times with different pigments of different color to provide the color filter with three primary color elements (red, green and blue). According to the printing method, one color element may be obtained by applying an ink composition consisting of the pigment of the present invention, a thermosetting resin such as polyamide resin or epoxy resin, and a solvent on the a basement, such as a glass plate, by means of a printer and then heating the same. The other conventional method may be employed to prepare the color filter comprising the pigment of the present invention.

Since the pigment of the present invention exhibits an excellent dispersibility and therefore, the color filter prepared by using the pigment exhibits an excellent spectral properties and small anti-polarization effect.

Since the pigment comprising the azo compound of the present invention exhibits an excellent charge generating ability, it may be used as a charge generating material of an organic photosensitive material used in an electrophotographic copier, a laser printer or the like. As a photosensitive material, function-divided organic photosensitive member composed of a charge generating material, which generates charge in response to light exposure and a charge transporting material, which transports the generated charge, both of them are dispersed in a binder resin.

Two types of organic photosensitive materials have been known, including so-called mono-layered type and laminated type. The pigment of the present invention may be applied for either type. The mono-layered type photosensitive member may be prepared by dissolving or dispersing a charge generating material and a charge transporting material in an appropriate solvent together with a binder resin and the like, applying the obtained solution or dispersion on an electrically conductive substrate and drying the same.

The laminated type photosensitive member may be prepared by applying a solution or a dispersion comprising a charge generating material and a binder resin on an electrically conductive substrate to provide a charge generating layer containing the charge generating material, and then applying a solution or a dispersion comprising a charge transporting material and a binder resin on the surface of the charge generating layer and then, drying the same. Alternatively, the charge transporting layer may be prepared on the electronic conductive substrate and the charge generating layer may be prepared over the same.

According to the present invention, the charge generating material comprises the pigment comprising the azo compound of the present invention, and other organic and inorganic photoconductive materials may be used in combination. Said photoconductive materials may include, for example, particles of an inorganic photoconductive material such as selenium, selenium-tellurium, selenium-aresenic, cadmium sulfide and amorphous-silicone, metal-free phthalocyanines, titanium phthalocyanines, perylene pigments, bisazo pigments, dithioketo pyrrolopyrrole pigments, metal-free naphthalocyanine pigments, metal-naphthalocyanine pigments, squarilium pigments, trisazo pigments, indigo pigments, azulenium pigments, cyanine pigments, and further, anthanthrone pigments, triphenylmethane pigments, surene pigments, toluidine pigments, pyrazoline pigments and quinacridone pigments. One or more of those charge generating materials may be selected depending on the region of photosensitive wavelength of the electrophotosensitive member.

Examples of the charge transporting materials may include tetracyano ethylene; fluorenone compounds such as 2,4,7-trinitro-9-fluolenone, fluorene compounds such as 9-carbazorylimino fluorene; nitro compounds such as dinitro anthracene; succinic anhydride, maleic anhydride; dibromo maleic anhydride; triphenylmethane compounds; oxadiazole compounds such as 2,5-di(4-dimethylaminophenyl)-1,3,4-oxadiazole; styryl compounds such as 9-(4-diethylaminostyryl) anthracene; carbazole compounds such as poly-N-vinyl carbazole; pyrazoline compounds such as 1-phenyl-3-(p-dimethylaminophenyl)pyrazoline; 4,4',4'-tris (N,N-diphenylamino)triphenylamine, amine derivatives such as 3,3'-dimethyl-N,N,N',N'-tetrakis-4-methylphenyl (1,1'-biphenyl)-4,4'-diamine; conjugated unsaturated compounds such as 1,1-bis(4-diethylaminophenyl)-4,4-diphenyl-1,3-butadiene; hydrazone compounds such as 4-(N,N-diethylamino)benzaldehyde-N,N-diphenylhydrazone; m-phenylenediamine compounds such as N,N,N',N'-tetrakis(3-tolyl)-1,3-phenylenediamine, N,N'-bis(4-tolyl)-N,N'-bis(3-tolyl)-1,3-phenylenediamine; nitrite containing compounds such as indole compounds, oxazole compounds, iso-oxazole compounds, thiazole compounds, thiadiazole compounds, imidazole compounds, pyrazole compounds, pyrazoline compounds, and triazole compounds; and condensed polycyclic compounds. Each of the charge transporting materials may be used by itself or in combination of two or more. When a charge generating material, such as polyvinyl carbazole, having film-forming property is used, the binder resin is not always necessary to add. Examples of the binder resins include thermoplastic resins, such as styrene polymers, styrene-butadiene copolymers, styrene-acrylonitrile copolymers, styrene-maleate copolymers, acrylic polymers, styrene-acrylic copolymers, polyethylene, ethylene-vinylacetate copolymers, polyethylene chlorides, polyvinyl chlorides, polypropylenes, vinyl chloride-vinyl acetate copolymers, polyesters, alkyd resins, polyamides, polyurethanes, polycarbonates, polyarylates, polysulfones, diallylphthalate resins, ketone resins, polyvinyl butyral resins, and polyether resins, thermosetting resins such as silicone resins, epoxy resins, phenol resins, urea resins, melamine resins and the other crosslinking resins, and photo-setting resins such as epoxy-acrylate and urethane-acrylate resins. The respective binder resins may be used by itself or in combination of two or more.

The photosensitive member may be incorporated with a various additives, for example, sensitizers, antioxidants, ultraviolet absorber, plastitizer, surfaceactive agent, leveling agent, and the like. Examples of the sensitizers may include terphenyl, halonaphtoquinones and acenaphthylene. Examples of the antioxidants may include phenol antioxidants such as 2,6-di-tert-butyl-p-cresol, triethyleneglycol-bis[3-(3-tert-butyl-5-methyl-4-hydroxy phenyl)propionate], 1,6-hexanediol-bis[3-(3,5-di-tert-butyl-4-hydroxyphenyl) propionate], pentaerythrithyl-tetrakis[3-(3,5-di-tert-butyl-4-hydroxyphenyl)propionate], 2,2-thio-diethylene bis[3-(3,5-di-tert-butyl-4-hydroxyphenyl)propionate], 2,2-thiobis(4-methyl-6-tert-butylphenol), N,N'-hexamethylene bis (3,5-di-tert-butyl-4-hydroxy-hydrocinnamide) and 1,3,5-trimethyl-2,4,6-tris(3,5-di-tert-butyl-4-hydroxybenzyl) benzene.

To prepare a laminated photosensitive member, the ratio of the charge generating material to the binder resin in the charge generating layer may vary and preferably be 5–1000 parts by weight, especially, 30–500 parts by weight of the charge generating material per 100 parts by weight of the binder resin.

The ratio of the charge transporting material to the binder resin in the charge transporting layer may vary within the range wherein the electronic charge transportation is not inhibited and crystallization is not induced. In order to facilitate the transportation of the charge generated in the charge generating layer, the total amount of the charge transporting material may be 10–500 parts by weight, especially, 25–200 parts by weight are admixed with 100 parts by weight of the binder resin.

As to the thickness of the laminated photosensitive member, the thickness of the charge generating layer may be about 0.01–5 $\mu$m, especially about 0.1–3$\mu$m, and that of the charge transporting layer may be about 2–100 $\mu$m, especially about 5–50 $\mu$m. For the mono-layered type photosensitive member, the amount of the charge generating material may suitably be 0.1–50 parts by weight, especially, 0.5–30 parts by weight and the total amount of the charge transporting material may be 20–500 parts by weight, especially, 30–200 parts by weight per 100 parts by weight of the binder resin.

The thickness of the photosensitive layer of the mono layered type may preferably be about 5–100 $\mu$m, especially, about 10–50 $\mu$m. The photosensitive member may have a barrier layer between the electrically conductive substrate and the photosensitive layer of the mono-layered type photosensitive member; or between the electrically conductive substrate and the charge generating layer, the electrically conductive substrate and the charge transporting layer, or charge generating layer and the charge transporting layer of the laminated type photosensitive member, in so far as the barrier does not impair the characteristic of the photosensitive member. The surface of the photosensitive member may be coated with a protective layer.

The electrically conductive substrate on which the above described layers are formed may be made from various materials having conductivity, for example, metals such as aluminum, copper, thin, platinum, silver, iron, vanadium, molybdenum, chromium, cadmium, titanium, nickel, palladium, indium, stainless steel, and brass, plastic materials on which surface is deposited or laminated with the above metals, and glass materials which is coated with aluminum iodide, tin oxide, indium oxide and the like.

The shape of the electrically conductive substrate may be any of sheet, drum and the like depending on the image forming devise in which the photosensitive member is applied. The substrate itself or the surface of the substrate is required to be electrically conductive. In addition, a substrate with a mechanical strength enough for use is preferable. When each of the layers consisting the photosensitive member is formed by coating, the above described charge generating materials, charge transporting materials, binder resins and others may be dissolved or dispersed into an appropriate solvent by means of a known method such as those using roll mill, ball mill, attritor, paint shaker, or ultrasonic disperser to give an coating material and then, said material may be applied on the surface and dried by means of a known manner.

A various organic solvents may be used for preparation of the coating material, for example, alcohols such as methanol, ethanol, isopropanol and butanol, aliphatic hydrocarbons such as n-hexane, octane and cyclohexane, aromatic hydrocarbons such as benzene, toluene and xylene, halogenated hydrocarbon such as dichloro methane, dichloro ethane, carbon tetrachloride and chlorobenzene, ethers such as dimethylether, diethylether, tetrahydrofuran, ethyleneglycoldimethylether, and diethyleneglycoldimethylether, ketones such as acetone, methylethyl ketone, and cyclohexanone, esters such as ethyl acetate and methyl acetate, dimethylformaldehyde, dimethylformamide, dimethylsulfoxide, and the like. These respective solvents may be used by itself or in combination of two or more.

The photosensitive member comprising the pigment of the present invention as a charge generating material exhibits high sensitivity and excellent properties such as lower residual potential.

Figure 1:
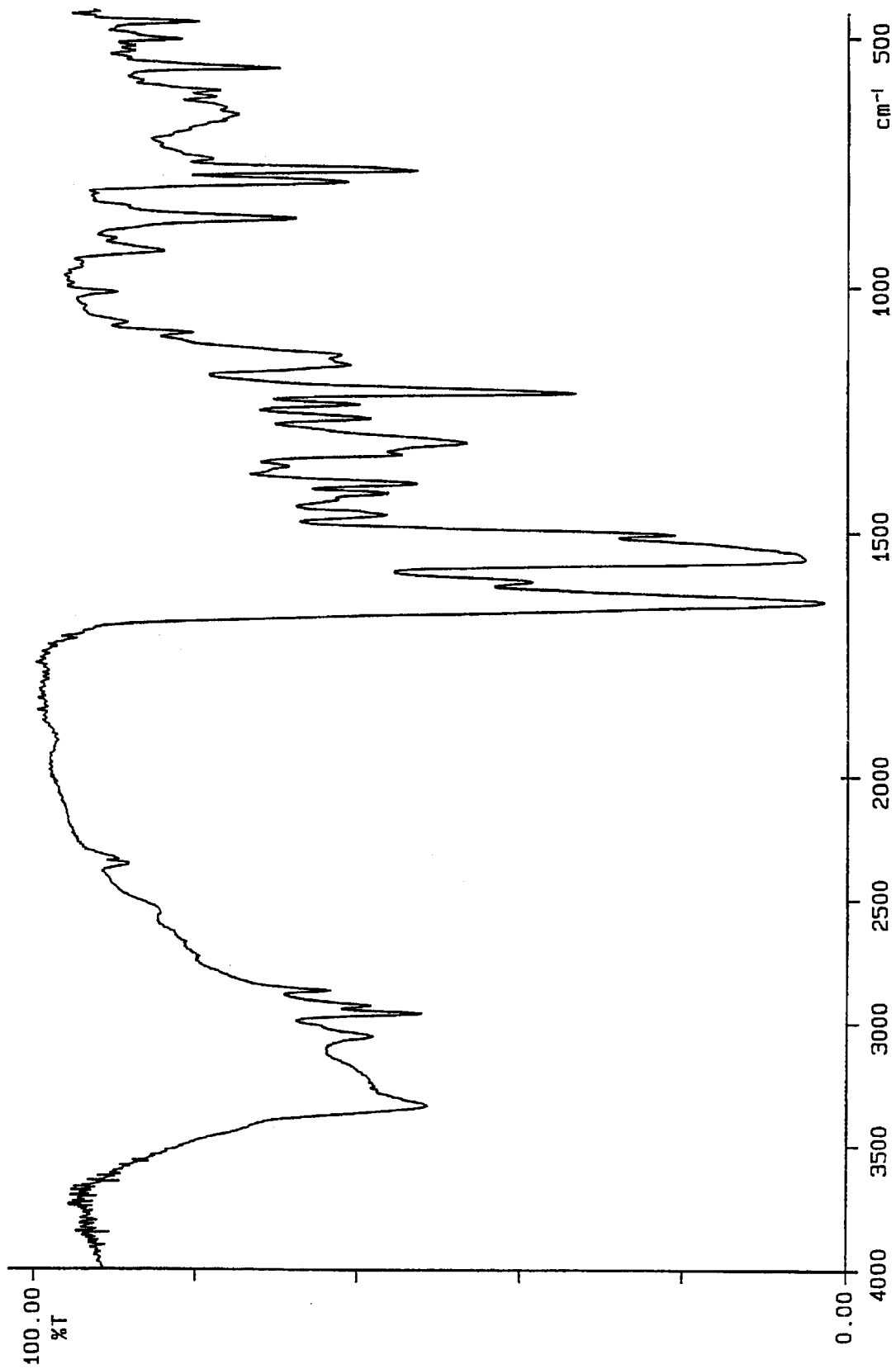
FIG. 1 shows an infrared absorption spectrum of the compound obtained in Example 1-1.

The invention is further illustrated by the following examples.

EXAMPLE 1-1

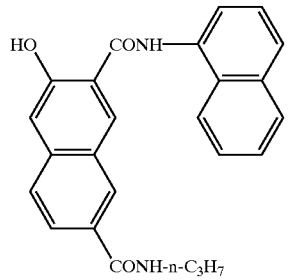

2-Hydroxy-3-hydroxycarbonyl-6-methoxy carbonyl naphthalene (36.9 g) was dispersed in 300 g of tetrahydrofuran, the mixture was added with 0.2 g of N,N-dimethylformamide and then 16.0 g of thionyl chloride, and reacted for two hours at 50° C. The residual thionyl chloride was removed together with the solvent by evaporation. To the remainder, 23.2 g of α-naphthylamine in 10 g of tetrahydrofuran, and then 25.2 g of 1,8-diazabicyclo[5.4.0] undec-7-ene were added and reacted under reflux for about 15 hours. Water (25.0 g) was added to the reacted mixture, and the precipitate was collected by filtration and then washed well with methanol and water. Thus obtained 2-hydroxy-6-methoxycarbonyl-3-(naphth-1'-yl) amino carbonyl naphthalene (37.2 g) was dispersed into 370 g of methanol, and 10.8 g of sodium hydroxide and 3.0 g of sodium carbonate in 150 g of water were added to the dispersion mixture. The obtained mixture was reacted at 70° C. for 2 hours and then, was treated with the active carbon and then adjusted the pH to 2. The precipitate was collected by filtration, washed well with water and dried to give 24.2 g of white gray powder.

Thus obtained 2-hydroxy-6-hydroxycarbonyl-3-(napht-1'-yl) aminocarbonyl naphthalene (6.0 g) was dispersed into 70 g of tetrahydrofuran, the mixture was added with 0.2 g of N,N-dimethylformamide and then 16.0 g of thionyl chloride, and reacted for two hours at 50° C. After the reaction, the residual thionyl chloride was removed together with the solvent by evaporation. To the remainder, 3.0 g of n-propylamine in 50 g of tetrahydrofuran and 7.6 g of 1,8-diazabicyclo[5.4.0]undec-7-ene were added and reacted under reflux for about 15 hours. After the concentration, 40 g of methanol, and then 5 g of hydrochloride were added to the residue and the precipitates were collected by filtration, washed well with water and methanol, and dried to give 3.0 g of white gray powder (decomposition point: 326° C.).

The infrared spectrum (by KBr method) of the composition is shown in FIG. 1.

EXAMPLE 1-2

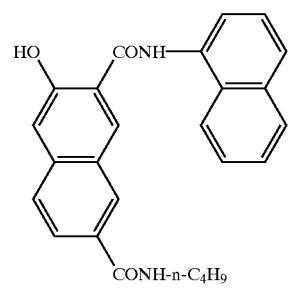

According to the same manner as described in Example 1-1 with the exception that 5.4 g of n-butylamine was used instead of n-propylamine, 3.6 g of white gray powder of the compound was obtained (decomposition point: 336° C.).

EXAMPLE 1-3

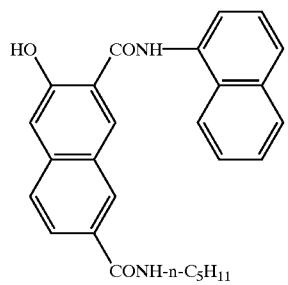

According to the same manner as described in Example 1-1 with the exception that 4.4 g of n-pentylamine was used instead of n-propylamine, 3.5 g of white gray powder of the compound was obtained (decomposition point: 326° C.).

EXAMPLE 1-4

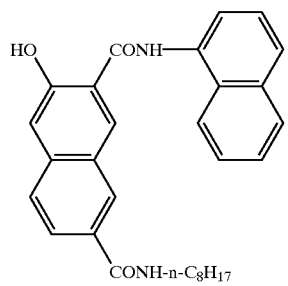

2-Hydroxy-6-hydroxycarbonyl-3-methoxycarbonyl naphthalene (36.9 g) was dispersed in 300 g of tetrahydrofuran, the mixture was added with 0.2 g of N,N-dimethylformamide and then 16.0 g of thionyl chloride, and reacted for two hours at 50° C. After the reaction, the residual thionyl chloride was removed together with the solvent by evaporation. To the remainder, 26.4 g of n-octylamine in 100 g of tetrahydrofuran, and then 25.2 g of 1,8-diazabicyclo[5.4.0]undec-7-ene were added and the mixture was reacted under reflux for about 15 hours. Water (250 g) was added to the reacted mixture and the precipitate was collected by filtration and then washed well with methanol and water. Thus obtained 2-hydroxy-3-methoxycarbonyl-6-n-octylaminocarbonyl naphthalene (38.7 g) was dispersed into 370 g of methanol, and 6.0 g of sodium hydroxide and 15.0 g of sodium carbonate in 200 g of water were added to the dispersion mixture. The obtained mixture was reacted at 70° C. for 2 hours and then, was treated with the active carbon and then adjusted the pH to 2. The precipitate was collected by filtration, washed well with water and dried to give 22.2 g of white gray powder.

Thus obtained 2-hydroxy-3-hydroxycarbonyl-6-n-octylaminocarbonyl naphthalene (5.9 g) was dispersed into 70 g of tetrahydrofuran, the mixture was added with 0.2 g of N,N-dimethylformamide and then 16.0 g of thionyl chloride, and reacted for two hours at 50° C. After the reaction, the residual thionyl chloride was removed together with the solvent by evaporation, 5.8 g of α-naphthylamine in 50 g of tetrahydrofuran and 7.6 g of 1,8-diazabicyclo[5.4.0]undec-7-ene were added to the remainder and reacted under reflux for about 15 hours. After the concentration, 40 g of methanol, and then 5 g of hydrochloride were added to the residue and the precipitates were collected by filtration, washed well with water and methanol, and dried to give 4.8 g of white gray powder (decomposition point: 342° C.).

EXAMPLE 1-5

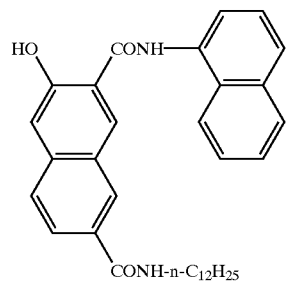

According to the same manner as described in Example 1-1 with the exception that 9.5 g of n-dodecyl amine was used instead of n-propylamine, 5.6 g of white gray powder of the compound was obtained (decomposition point: 347° C.).

EXAMPLE 1-6

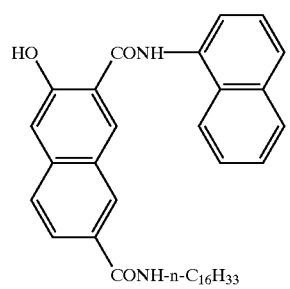

According to the same manner as described in Example 1-1 with the exception that 12.3 g of n-hexadecyl amine was used instead of n-propylamine, 7.7 g of white gray powder of the compound was obtained (decomposition point: 368° C.).

EXAMPLE 1-7

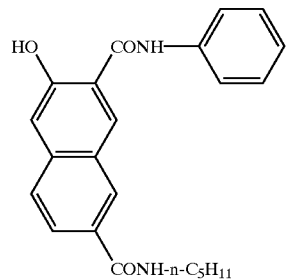

According to the same manner as described in Example 1-1 with the exception that 15.1 g of aniline was used instead of α-naphthylamine and 4.4 g of n-pentylamine was used instead of n-propylamine, 4.5 g of white powder of the compound was obtained (decomposition point: 255° C.).

EXAMPLE 1-8

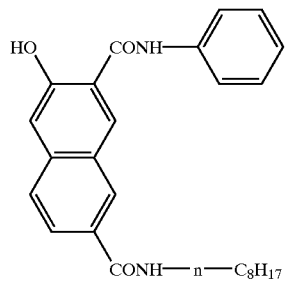

According to the same manner as described in Example 1-1 with the exception that 15.1 g of aniline was used instead of α-naphthylamine and 5.2 g of n-octylamine was used instead of n-propylamine, 3.0 g of white powder of the compound was obtained (decomposition point: 273° C.).

EXAMPLE 1-9

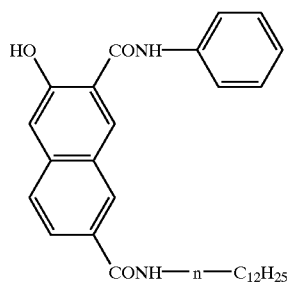

According to the same manner as described in Example 1-1 with the exception that 15.1 g of aniline was used instead of α-naphthylamine and 7.4 g of n-dodecylamine was used instead of n-propylamine, 4.1 g of white powder of the compound was obtained (decomposition point: 264° C.).

EXAMPLE 1-10

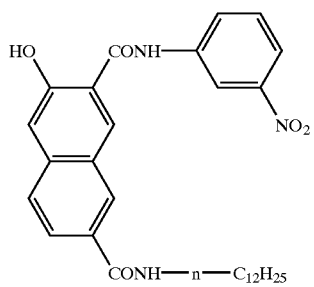

According to the same manner as described in Example 1-1 with the exception that 21.6 g of 3-nitroaniline was used instead of α-naphthylamine and 7.4 g of n-dodecylamine was used instead of n-propylamine, 6.8 g of white powder of the compound was obtained (decomposition point: 302° C.).

EXAMPLE 1-11

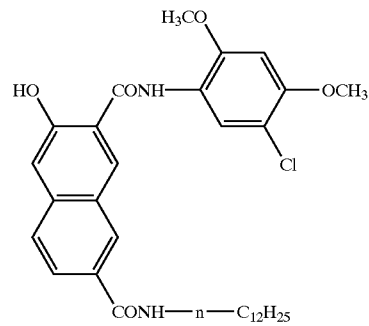

According to the same manner as described in Example 1-1 with the exception that 30.4 g of 5-chrolo-2,4-dimethoxyaniline was used instead of α-naphthylamine and 7.4 g of n-dodecylamine was used instead of n-propylamine, 6.5 g of white powder of the compound was obtained (decomposition point: 247° C.).

EXAMPLE 1-12

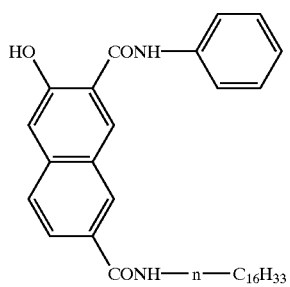

According to the same manner as described in Example 1-1 with the exception that 15.1 g of aniline was used instead of α-naphthylamine and 9.2 g of n-hexadecylamine was used instead of n-propylamine, 3.8 g of white powder of the compound was obtained (decomposition point: 257° C.).

EXAMPLE 1-13

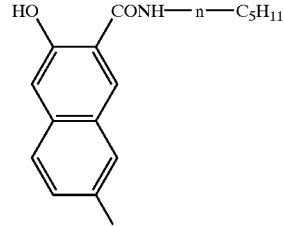

2-Hydroxy-3,6-dihydroxycarbonyl naphthalene (18.6 g) was dispersed in 200 g of tetrahydrofuran, the mixture was added with 0.2 g of N,N-dimethylformamide and then 38.0 g of thionyl chloride, and reacted for about 15 hours at 50° C. After the reaction, the residual thionyl chloride was removed together with the solvent by evaporation. To the remainder, 8.7 g of n-pentylamine in 50 g of tetrahydrofuran, and then 15.2 g of 1,8-diazabicyclo[5.4.0]undec-7-ene were added and reacted under reflux for about 15 hours. After the concentration, 20 g of methanol, and then 50 g of water were added to the residue. The precipitates were collected by filtration, washed well with water and methanol, and dried to give 2.6 g of white gray powder (decomposition point: 345° C.).

EXAMPLE 1-14

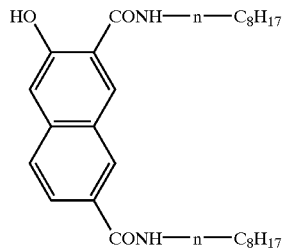

According to the same manner as described in Example 1-13 with the exception that 12.9 g of n-octylamine was used instead of n-pentylamine, 1.6 g of white gray powder of the compound was obtained (decomposition point: 366° C.).

EXAMPLE 1-15

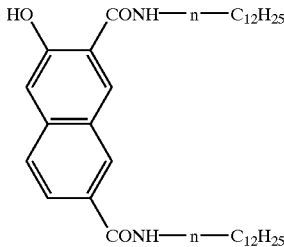

According to the same manner as described in Example 1-13 with the exception that 18.5 g of n-dodecylamine was used instead of n-pentylamine, 3.3 g of white gray powder of the compound was obtained (decomposition point: 383° C.).

EXAMPLE 1-16

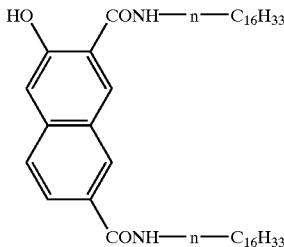

According to the same manner as described in Example 1-13 with the exception that 24.1 g of n-hexadecylamine was used instead of n-pentylamine, 11.2 g of white gray powder of the compound was obtained (decomposition point: 397° C.).

EXAMPLE 1-17

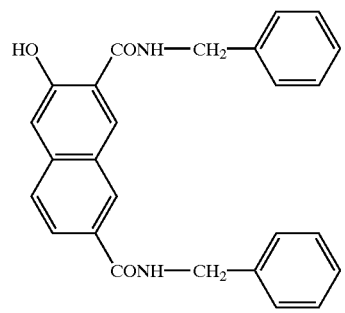

According to the same manner as described in Example 1-13 with the exception that 10.7 g of benzylamine was used instead of n-pentylamine, 3.0 g of white gray powder of the compound was obtained (melting point: 237° C.).

EXAMPLE 1-18

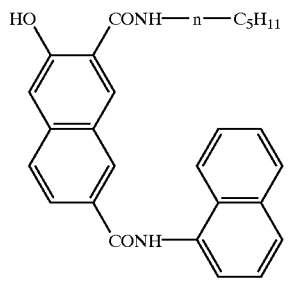

According to the same manner as described in Example 1-1 with the exception that 2-hydroxy-3-hydroxycarbonyl-6-(naphth-1'-yl) aminocarbonyl naphthalene, which was obtained by using 2-hydroxy-6-hydroxycarbonyl-3-methoxycarbonyl naphthalene instead of 2-hydroxy-3-hydroxycarbonyl-6-methoxycarbonyl naphthalene, was used and 4.4 g of n-pentylamine was used instead of n-propylamine, 3.0 g of white gray powder of the compound was obtained (decomposition point: 345° C.).

EXAMPLE 1-19

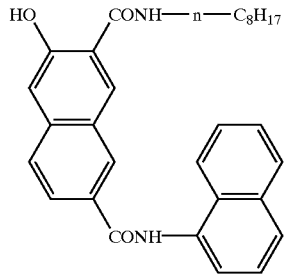

According to the same manner as described in Example 1-1 with the exception that 2-hydroxy-3-hydroxycarbonyl-6-(naphth-1'-yl) aminocarbonyl naphthalene, which was obtained by using 2-hydroxy-6-hydroxycarbonyl-3-methoxycarbonyl naphthalene instead of 2-hydroxy-3-hydroxycarbonyl-6-methoxycarbonyl naphthalene, was used, and 6.6 g of n-octylamine was used instead of n-propylamine, 4.0 g of white gray powder of the compound was obtained (decomposition point: 346° C.).

EXAMPLE 1-20

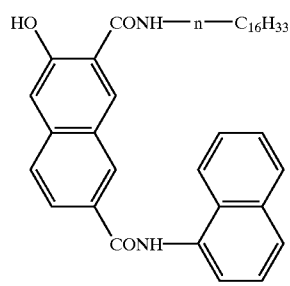

According to the same manner as described in Example 1-1 with the exception that 2-hydroxy-3-hydroxycarbonyl-6-(naphth-1'-yl) aminocarbonyl naphthalene, which was obtained by using 2-hydroxy-6-hydroxycarbonyl-3-methoxycarbonyl naphthalene instead of 2-hydroxy-3-hydroxycarbonyl-6-methoxycarbonyl naphthalene was used, and 12.3 g of n-hexadecylamine was used instead of n-propylamine, 3.6 g of white gray powder of the compound was obtained (decomposition point: 366° C.)

EXAMPLE 1-21

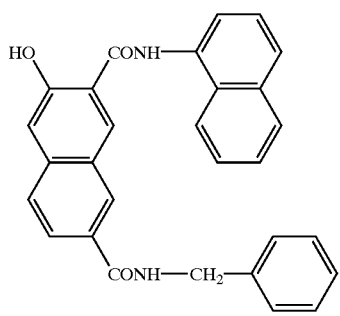

According to the same manner as described in Example 1-1 with the exception that 5.5 g of benzylamine was used instead of n-propylamine, 3.2 g of white powder of the compound was obtained (melting point: 236° C.).

EXAMPLE 1-22

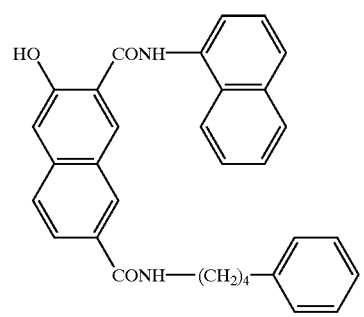

According to the same manner as described in Example 1-1 with the exception that 7.6 g of 4-phenylbutylamine was used instead of n-propylamine, 4.7 g of white gray powder of the compound was obtained (melting point: 205° C.).

EXAMPLE 1-23–EXAMPLE 1-34

Coupler compounds of the examples were synthesized according to the same manner as described in Example 1-1 with the exception that amines shown in the tables 1 and 2 were used instead of n-propylamine. Decomposition points of thus synthesized coupler compounds are shown in the tables 1 and 2.

TABLE 1

| example No. | amine component | structure of coupler compound | decomposition point |
|---|---|---|---|
| 1-23 | $H_2NC_3H_6$—N⟨⟩O | HO–[naphthalene]–CONH–[naphthalene]; CONHC_3H_6—N⟨⟩O | 301° C. |

TABLE 1-continued

| example No. | amine component | structure of coupler compound | decomposition point |
|---|---|---|---|
| 1-24 | H₂N–cyclohexyl(H) | 3-hydroxy-N,N'-bis(cyclohexyl)naphthalene-2,7-dicarboxamide (one amide to 1-naphthyl, other to cyclohexyl-H) | 335° C. |
| 1-25 | H₂NCH₂–(3-pyridyl) | 3-hydroxy-N-(1-naphthyl)-N'-(3-pyridylmethyl)naphthalene-2,7-dicarboxamide | 330° C. |
| 1-26 | H₂NC₂H₄–phenyl | 3-hydroxy-N-(1-naphthyl)-N'-(2-phenylethyl)naphthalene-2,7-dicarboxamide | 343° C. |
| 1-27 | H₂NC₂H₄–C₆H₄–OCH₃ | 3-hydroxy-N-(1-naphthyl)-N'-[2-(4-methoxyphenyl)ethyl]naphthalene-2,7-dicarboxamide | 344° C. |

TABLE 1-continued

| example No. | amine component | structure of coupler compound | decomposition point |
|---|---|---|---|
| 1-28 | H₂NCH₂—CH(C₂H₅)—C₄H₉ | HO-naphthalene-CONH-naphthyl, CONHCH₂—CH(C₂H₅)—C₄H₉ | 337° C. |
| 1-29 | H₂NC₃H₆OCH₂—CH(C₂H₅)—C₄H₉ | HO-naphthalene-CONH-naphthyl, CONHC₃H₆OCH₂—CH(C₂H₅)—C₄H₉ | 335° C. |

TABLE 2

| example No. | amine component | structure of coupler compound | decomposition point |
|---|---|---|---|
| 1-30 | H₂NCH₂-furyl | HO-naphthalene-CONH-naphthyl, CONHCH₂-furyl | 312° C. |
| 1-31 | H₂N—C(CH₃)₃ | HO-naphthalene-CONH-naphthyl, CONHC(CH₃)₃ | 278° C. |

TABLE 2-continued

| example No. | amine component | structure of coupler compound | decomposition point |
|---|---|---|---|
| 1-32 | H₂NC₃H₆NH-⟨⟩-H | (structure shown) | 291° C. |
| 1-33 | H₂NC₃H₆Si(OC₂H₅)₃ | (structure shown) | 307° C. |
| 1-34 | H₂NC₂H₄NHC₃H₆Si(OCH₃)₃ | (structure shown) | 258° C. |

EXAMPLE 1-35

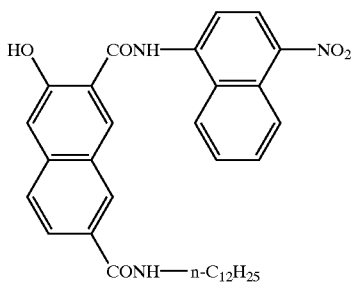

2-Hydroxy-6-hydroxycarbonyl-3-methoxy carbonyl naphthalene (36.9 g) was dispersed in 300 g of tetrahydrofuran, the mixture was added with 0.2 g of N,N-dimethylformamide and then 16.0 g of thionyl chloride, and reacted for two hours at 50° C. The residual thionyl chloride was removed together with the solvent by evaporation. To the remainder, 33.4 g of n-dodecylamine in 10 g of tetrahydrofuran and the mixture was reacted under reflux for about 15 hours. Water(250 g) was added to the reacted mixture, and the precipitate was collected by filtration and then washed well with methanol and water. Thus obtained 2-hydroxy-3-methoxycarbonyl-6-(n-dodecylaminocarbonyl) naphthalene (43.4 g) was dispersed into 370 g of methanol, and 10.8 g of sodium hydroxide and 3.0 g of sodium carbonate in 150 g of water were added to the dispersion mixture. The obtained mixture was reacted at 70° C. for 2 hours and then, was treated with the active carbon and then adjusted the pH to 2. The precipitate was collected by filtration, washed well with water and dried to give 37.2 g of white gray powder.

Thus obtained 2-hydroxy-3-hydroxycarbonyl-6-(n-dodecylaminocarbonyl) naphthalene (5.0 g) was dispersed into 60 g of tetrahydrofuran, the mixture was added with 0.1 g of N,N-dimethylformamide and then 2.5 g of thionyl chloride, and reacted for about 1 hour at 50° C. After the reaction, the residual thionyl chloride was removed together with the solvent by evaporation. To the remainder, 5.3 g of 4-nitro-1-naphthylamine in 50 g of tetrahydrofuran was added and the mixture was reacted under reflux for about 15 hours. After the concentration, 40 g of methanol was added to the residue and the precipitates were collected by filtration, washed well with water and methanol, and dried to give 4.8 g of white gray powder (decomposition point: 281° C.).

EXAMPLE 1-36–EXAMPLE 1-52

Coupler compounds of the examples were synthesized according to the same manner as described in Example 1-35 with the exception that amines shown in the tables 3–5 were used instead of 4-nitro-1-naphthylamine. Decomposition points of thus synthesized coupler compounds are shown in the tables 3–5.

TABLE 3

| example No. | amine component | structure of coupler compound | decomposition point |
|---|---|---|---|
| 1-36 | | | 229° C. |
| 1-37 | | | 341° C. |
| 1-38 | | | 352° C. |
| 1-39 | | | 340° C. |
| 1-40 | | | 353° C. |

TABLE 3-continued

| example No. | amine component | structure of coupler compound | decomposition point |
|---|---|---|---|
| 1-41 | [3-aminopyrene structure] | [3-hydroxy-N-(pyren-1-yl)-6-(dodecylcarbamoyl)naphthalene-2-carboxamide structure] | 356° C. |
| 1-42 | [4-amino-2-methylquinoline structure] | [3-hydroxy-N-(2-methylquinolin-4-yl)-6-(dodecylcarbamoyl)naphthalene-2-carboxamide structure] | 346° C. |

TABLE 4

| example No. | amine component | structure of coupler compound | decomposition point |
|---|---|---|---|
| 1-43 | [1-aminoanthraquinone structure] | [3-hydroxy-N-(9,10-dioxoanthracen-1-yl)-6-(dodecylcarbamoyl)naphthalene-2-carboxamide structure] | 346° C. |
| 1-44 | [2-aminoanthraquinone structure] | [3-hydroxy-N-(9,10-dioxoanthracen-2-yl)-6-(dodecylcarbamoyl)naphthalene-2-carboxamide structure] | 347° C. |

TABLE 4-continued

| example No. | amine component | structure of coupler compound | decomposition point |
|---|---|---|---|
| 1-45 | 2-chloroaniline | 3-hydroxy-N-(2-chlorophenyl)-7-(N-n-dodecylcarbamoyl)-2-naphthamide | 332° C. |
| 1-46 | o-toluidine | 3-hydroxy-N-(2-methylphenyl)-7-(N-n-dodecylcarbamoyl)-2-naphthamide | 343° C. |
| 1-47 | 4-phenoxyaniline | 3-hydroxy-N-(4-phenoxyphenyl)-7-(N-n-dodecylcarbamoyl)-2-naphthamide | 352° C. |
| 1-48 | 4-amino-2,5-dimethoxy-N-phenylbenzamide | 3-hydroxy-N-[2,5-dimethoxy-4-(N-phenylcarbamoyl)phenyl]-7-(N-n-dodecylcarbamoyl)-2-naphthamide | 348° C. |

TABLE 4-continued

| example No. | amine component | structure of coupler compound | decomposition point |
|---|---|---|---|
| 1-49 | 2-methoxyaniline (H₃CO, H₂N-phenyl) | 3-hydroxy-N-(2-methoxyphenyl)-7-(n-dodecylcarbamoyl)-2-naphthamide | 353° C. |

TABLE 5

| example No. | amine component | structure of coupler compound | decomposition point |
|---|---|---|---|
| 1-50 | 2-ethoxyaniline (C₂H₅O, H₂N-phenyl) | 3-hydroxy-N-(2-ethoxyphenyl)-7-(n-dodecylcarbamoyl)-2-naphthamide | 349° C. |
| 1-51 | 5-amino-benzimidazol-2(3H)-one | 3-hydroxy-N-(2-oxo-2,3-dihydro-1H-benzimidazol-5-yl)-7-(n-dodecylcarbamoyl)-2-naphthamide | 383° C. |
| 1-52 | 3-amino-4-methoxy-N-phenylbenzamide | 3-hydroxy-N-(2-methoxy-5-(phenylcarbamoyl)phenyl)-7-(n-dodecylcarbamoyl)-2-naphthamide | 346° C. |

EXAMPLE 1-53

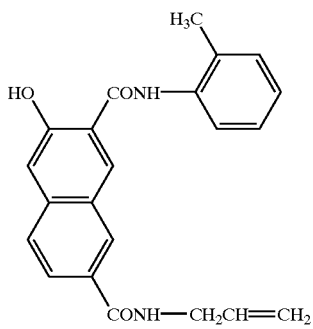

According to the same manner as described in Example 1-1 with the exception that 17.4 g of o-toluidine was used instead of α-naphthylamine, and 2.3 g of allylamine was used instead of n-propylamine, 4.8 g of white powder of the compound was obtained (melting point: 234° C.).

EXAMPLE 1-54

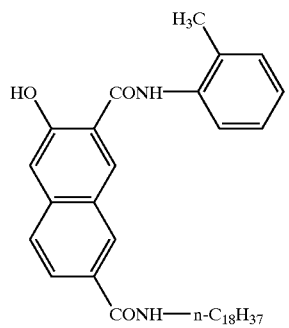

According to the same manner as described in Example 1-1 with the exception that 17.4 g of o-toluidine was used instead of α-naphthylamine, and 10.8 g of n-octadecylamine (stearyl amine) was used instead of n-propylamine, 5.1 g of white powder of the compound was obtained (melting point: 186° C.).

EXAMPLE 2-1

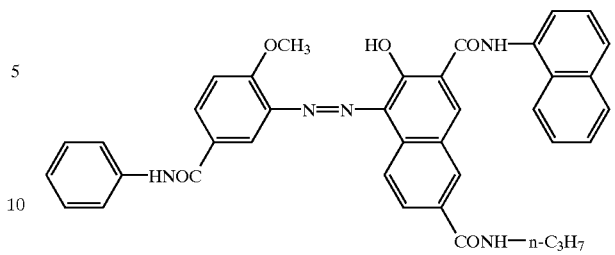

As an amine component, 2.9 g of 2-methoxy-5-phenylaminocarbonylaniline was dispersed into 45 g of water and added with 4.3 g of 35% aqueous hydrochloride. Then 1.0 g of sodium nitrite in 10 g of water was added dropwise to the mixture at 0–5° C. to conduct diazotization. Then, 0.8 g of acetic acid, 0.15 g of filtration assistant, and 0.15 g of charcoal were added and the mixture was filtrated. The temperature was kept below 10° C. After that, 6 g of 42% aqueous tetrafluoroboric acid was added to the filtrate and the precipitated diazonium salt was obtained by filtration. On the other hand, as a coupler component, 3.4 g of the compound obtained in Example 1-1 was dispersed into 60 g of N-methyl-2-pyrrolidone, 0.9 g of sodium methoxide was added to the mixture to dissolve, and the solution was kept at 15° C. The above obtained diazonium salt (4.1 g) in 15 g of N-methyl-2-pyrrolidone was added to the solution and stirred for about 15 hours. Then, 1.2 g of acetic acid was added to the reaction mixture and stirred for 1 hour, then 40 g of water was added to the mixture and the precipitate was collected by filtration. Thus obtained solid material was washed in 120 g of methanol under reflux and filtrated. The solid material was further washed in 60 g of pyridine under reflux, filtrated, washed well with methanol, and dried to give 4.2 g of reddish purple powder (decomposition point: 330° C.).

Figure 2:
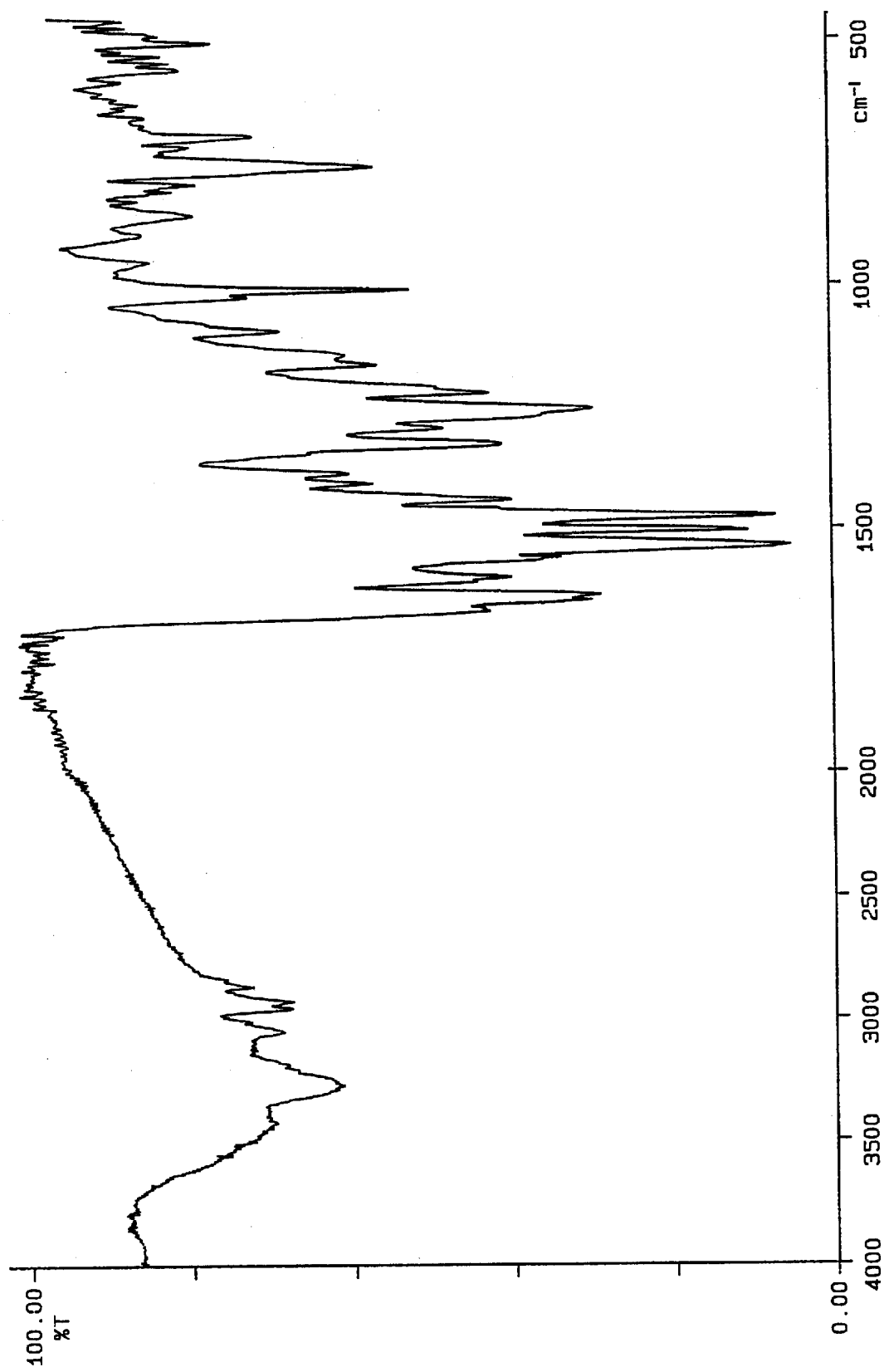
FIG. 2 shows an infrared absorption spectrum of the compound obtained in Example 2-1.

The infrared spectrum (by KBr method) of the composition is shown in FIG. 2.

EXAMPLE 2-2–EXAMPLE 2-87

Azo compounds of the examples were synthesized according to the same manner as Example 2-1 with the exception that amines shown in the tables 6–27 were used instead of 2-methoxy-5-phenylaminocarbonyl aniline, and couplers shown in the tables 6–27 were used instead of the compound obtained in the Example 1-1. Decomposition points of thus synthesized azo compounds are shown in the tables 6–27.

TABLE 6

| example No. | amine component | coupler component | structure of azo compound | color | decomposition point |
|---|---|---|---|---|---|
| 2-2 | (OCH₃, HNOC-phenyl, NH₂) | example 1-2 | (structure shown) | reddish purple | 335° C. |

TABLE 6-continued

| example No. | amine component | coupler component | structure of azo compound | color | decomposition point |
|---|---|---|---|---|---|
| 2-3 | 3-amino-4-methoxy-N-phenylbenzamide | example 1-3 | (azo compound with OCH₃, HNOC-Ph, naphthol, CONH-naphthyl, CONH—n-$C_5H_{11}$) | dark bluish red | 325° C. |
| 2-4 | 3-amino-4-methoxy-N-phenylbenzamide | example 1-4 | (azo compound with OCH₃, HNOC-Ph, naphthol, CONH-naphthyl, CONH—n-$C_8H_{17}$) | reddish purple | 326° C. |
| 2-5 | 3-amino-4-methoxy-N-phenylbenzamide | example 1-5 | (azo compound with OCH₃, HNOC-Ph, naphthol, CONH-naphthyl, CONH—n-$C_{12}H_{25}$) | reddish purple | 317° C. |

TABLE 7

| example No. | amine component | coupler component | structure of azo compound | color | decomposition point |
|---|---|---|---|---|---|
| 2-6 | 3-amino-4-methoxy-N-phenylbenzamide | example 1-6 | (azo compound with OCH₃, HNOC-Ph, naphthol, CONH-naphthyl, CONH—n-$C_{16}H_{33}$) | reddish purple | 313° C. |

TABLE 7-continued

| example No. | amine component | coupler component | structure of azo compound | color | decomposition point |
|---|---|---|---|---|---|
| 2-7 | (4-methoxy-3-amino-N-phenylbenzamide) | example 1-7 | azo compound structure with OCH₃, HNOC-phenyl, HO, CONH-phenyl, CONH—n-C₅H₁₁ | bright bluish red | 271° C. |
| 2-8 | (4-methoxy-3-amino-N-phenylbenzamide) | example 1-8 | azo compound structure with OCH₃, HNOC-phenyl, HO, CONH-phenyl, CONH—n-C₈H₁₇ | bright red | 285° C. |
| 2-9 | (4-methoxy-3-amino-N-phenylbenzamide) | example 1-9 | azo compound structure with OCH₃, HNOC-phenyl, HO, CONH-phenyl, CONH—n-C₁₂H₂₅ | bright red | 284° C. |

TABLE 8

| example No. | amine component | coupler component | structure of azo compound | color | decomposition point |
|---|---|---|---|---|---|
| 2-10 | (4-methoxy-3-amino-N-phenylbenzamide) | example 1-10 | azo compound structure with OCH₃, HNOC-phenyl, HO, CONH-(3-nitrophenyl), NO₂, CONH—n-C₁₂H₂₅ | dark bluish red | 301° C. |

TABLE 8-continued

| example No. | amine component | coupler component | structure of azo compound | color | decomposition point |
|---|---|---|---|---|---|
| 2-11 | 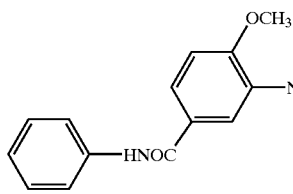 | example 1-11 | 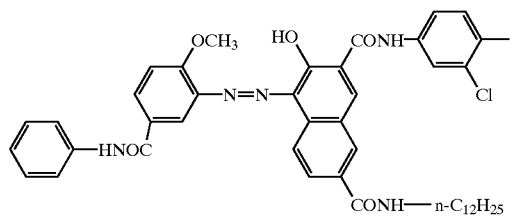 | reddish purple | 328° C. |
| 2-12 | 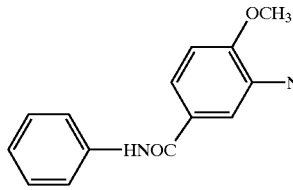 | example 1-12 | 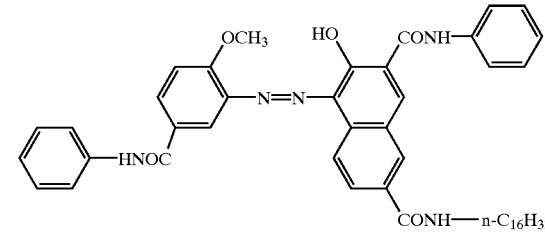 | bright red | 266° C. |
| 2-13 | 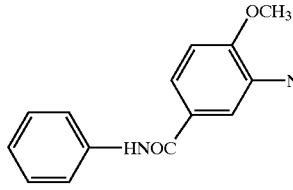 | example 1-13 | 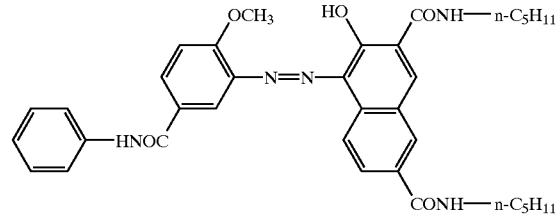 | bright bluish red | 294° C. |

TABLE 9

| example No. | amine component | coupler component | structure of azo compound | color | decomposition point |
|---|---|---|---|---|---|
| 2-14 | 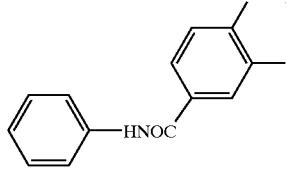 | example 1-14 | 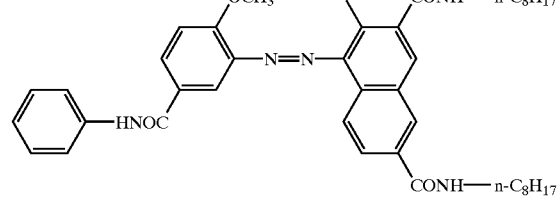 | bright yellowish orange | 374° C. |
| 2-15 | 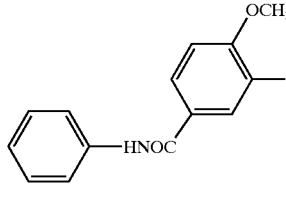 | example 1-15 | 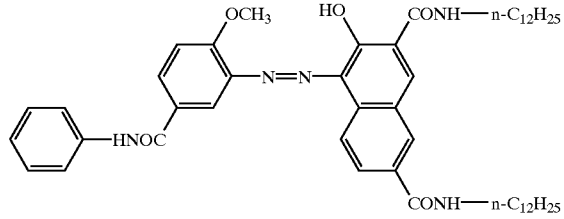 | bright orange | 284° C. |

TABLE 9-continued

| example No. | amine component | coupler component | structure of azo compound | color | decomposition point |
|---|---|---|---|---|---|
| 2-16 | (structure with OCH₃, NH₂, -HNOC-phenyl) | example 1-16 | (azo compound structure with OCH₃, HO, CONH—n-C₁₆H₃₃, CONH—n-C₁₆H₃₃) | bright reddish orange | 269° C. |
| 2-17 | (structure with OCH₃, NH₂, -HNOC-phenyl) | example 1-17 | (azo compound structure with OCH₃, HO, CONH-CH₂-phenyl, CONH-CH₂-phenyl) | reddish orange | 309° C. |

TABLE 10

| example No. | amine component | coupler component | structure of azo compound | color | decomposition point |
|---|---|---|---|---|---|
| 2-18 | (structure with OCH₃, NH₂, -HNOC-phenyl) | example 1-18 | (azo compound with OCH₃, HO, CONH—n-C₅H₁₁, CONH-naphthyl) | dark brownish red | 308° C. |
| 2-19 | (structure with OCH₃, NH₂, -HNOC-phenyl) | example 1-19 | (azo compound with OCH₃, HO, CONH—n-C₈H₁₇, CONH-naphthyl) | brownish red | 301° C. |

TABLE 10-continued

| example No. | amine component | coupler component | structure of azo compound | color | decomposition point |
|---|---|---|---|---|---|
| 2-20 | (4-methoxy-3-amino-N-phenylbenzamide) | example 1-20 | | reddish orange | 289° C. |
| 2-21 | (4-methoxy-3-amino-N-phenylbenzamide) | example 1-21 | | dark bluish red | 325° C. |

TABLE 11

| example No. | amine component | coupler component | structure of azo compound | color | decomposition point |
|---|---|---|---|---|---|
| 2-22 | (4-methoxy-3-amino-N-phenylbenzamide) | example 1-22 | | reddish purple | 322° C. |
| 2-23 | (2-methoxy-4-nitroaniline) | example 1-5 | | reddish purple | 304° C. |

TABLE 11-continued

| example No. | amine component | coupler component | structure of azo compound | color | decomposition point |
|---|---|---|---|---|---|
| 2-24 | 4-chloro-2-methylaniline | example 1-5 | azo compound with 4-chloro-2-methylphenyl diazo, 3-hydroxy-N-(1-naphthyl)-2-naphthamide, 6-CONH-n-C₁₂H₂₅ | bluish red | 292° C. |
| 2-25 | 3-chloroaniline | example 1-5 | azo compound with 3-chlorophenyl diazo, 3-hydroxy-N-(1-naphthyl)-2-naphthamide, 6-CONH-n-C₁₂H₂₅ | reddish orange | 287° C. |

TABLE 12

| example No. | amine component | coupler component | structure of azo compound | color | decomposition point |
|---|---|---|---|---|---|
| 2-26 | 2-(ethoxycarbonyl)aniline | example 1-5 | azo compound with 2-(C₂H₅OOC)phenyl diazo, 3-hydroxy-N-(1-naphthyl)-2-naphthamide, 6-CONH-n-C₁₂H₂₅ | brown | 309° C. |
| 2-27 | 2-(trifluoromethyl)aniline | example 1-5 | azo compound with 2-CF₃-phenyl diazo, 3-hydroxy-N-(1-naphthyl)-2-naphthamide, 6-CONH-n-C₁₂H₂₅ | dark brown | 291° C. |

TABLE 12-continued

| example No. | amine component | coupler component | structure of azo compound | color | decomposition point |
|---|---|---|---|---|---|
| 2-28 | phenylamine (C₆H₅-NH₂) | example 1-5 | [azo compound structure with phenyl-N=N, HO, CONH-naphthyl, CONH-n-C₁₂H₂₅] | reddish orange | 292° C. |
| 2-29 | 2,5-dichloroaniline | example 1-5 | [azo compound structure with 2,5-dichlorophenyl-N=N, HO, CONH-naphthyl, CONH-n-C₁₂H₂₅] | brownish red | 301° C. |

TABLE 13

| example No. | amine component | coupler component | structure of azo compound | color | decomposition point |
|---|---|---|---|---|---|
| 2-30 | 2-methyl-5-nitroaniline | example 1-5 | [azo compound structure with 2-methyl-5-nitrophenyl-N=N, HO, CONH-naphthyl, CONH-n-C₁₂H₂₅] | yellowish red | 291° C. |
| 2-31 | 4-chloro-2-nitroaniline | example 1-5 | [azo compound structure with 4-chloro-2-nitrophenyl-N=N, HO, CONH-naphthyl, CONH-n-C₁₂H₂₅] | dark purple | 304° C. |

TABLE 13-continued

| example No. | amine component | coupler component | structure of azo compound | color | decomposition point |
|---|---|---|---|---|---|
| 2-32 | (2-methoxy-5-diethylsulfamoyl aniline) | example 1-5 | azo compound with OCH₃, Et₂NO₂S, HO, CONH-naphthyl, CONH-n-C₁₂H₂₅ | bright red | 301° C. |
| 2-33 | (4-methoxy-3-amino-N-phenylbenzamide) | example 1-23 | azo compound with OCH₃, PhHNOC, HO, CONH-naphthyl, CONHC₃H₆-N-piperidine | reddish purple | 329° C. |

TABLE 14

| example No. | amine component | coupler component | structure of azo compound | color | decomposition point |
|---|---|---|---|---|---|
| 2-34 | (4-methoxy-3-amino-N-phenylbenzamide) | example 1-24 | azo compound with OCH₃, PhHNOC, HO, CONH-naphthyl, CONH-cyclohexyl | reddish purple | 269° C. |
| 2-35 | (4-methoxy-3-amino-N-phenylbenzamide) | example 1-25 | azo compound with OCH₃, PhHNOC, HO, CONH-naphthyl, CONHCH₂-pyridyl | dark brown | 313° C. |

TABLE 14-continued

| example No. | amine component | coupler component | structure of azo compound | color | decomposition point |
|---|---|---|---|---|---|
| 2-36 | (4-methoxy-3-amino-phenyl with -HNOC-phenyl) | example 1-26 | (azo compound structure) | dark brown | 315° C. |
| 2-37 | (4-methoxy-3-amino-phenyl with -HNOC-phenyl) | example 1-27 | (azo compound structure) | reddish purple | 279° C. |

TABLE 15

| example No. | amine component | coupler component | structure of azo compound | color | decomposition point |
|---|---|---|---|---|---|
| 2-38 | (2-amino-4-(phenylcarbamoyl)-1-methoxybenzene) | example 1-28 | azo compound structure with naphthalene, OCH₃, CONH-naphthyl, OH, and CONHCH₂-CH(C₂H₅)-C₄H₉ groups | bluish red | 324° C. |
| 2-39 | (2-amino-4-(phenylcarbamoyl)-1-methoxybenzene) | example 1-29 | azo compound structure with naphthalene, OCH₃, CONH-naphthyl, OH, and CONHC₃H₆OCH₂-CH(C₂H₅)-C₄H₉ groups | bluish red | 329° C. |

TABLE 15-continued

| example No. | amine component | coupler component | structure of azo compound | color | decomposition point |
|---|---|---|---|---|---|
| 2-40 | (structure with OCH₃, NH₂, CONH-phenyl) | example 1-30 | (azo compound structure with naphthyl-CONH, HO, OCH₃, N=N, CONHCH₂-furyl, CONH-phenyl) | dark bluish red | 306° C. |
| 2-41 | (structure with OCH₃, NH₂, CONH-phenyl) | example 1-31 | (azo compound structure with naphthyl-CONH, HO, OCH₃, N=N, CONHC(CH₃)₃, CONH-phenyl) | bluish red | 314° C. |

TABLE 16
| example No. | amine component | coupler component | structure of azo compound | color | decomposition point |
|---|---|---|---|---|---|
| 2-42 | 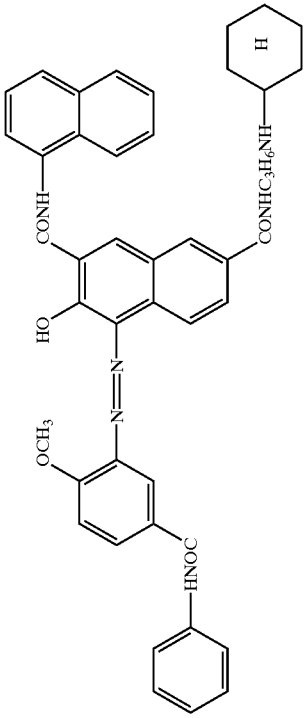 | example 1-32 | | dark bluish red | 242° C. |
| 2-43 | 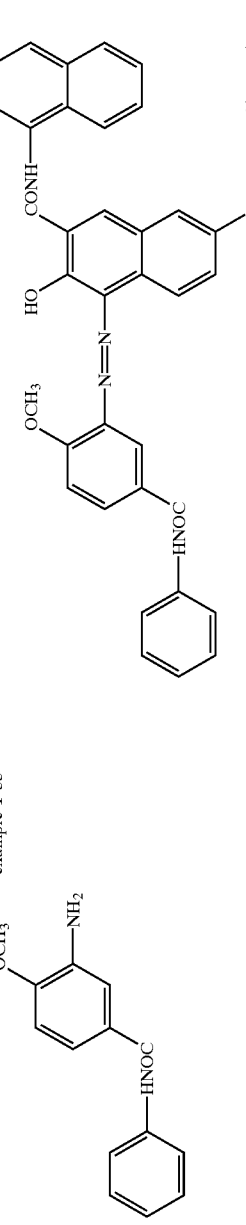 | example 1-33 | | reddish purple | 323° C. |

TABLE 16-continued

| example No. | amine component | coupler component | structure of azo compound | color | decomposition point |
|---|---|---|---|---|---|
| 2-44 | OCH₃, NH₂, CONH-phenyl | example 1-34 | azo compound with CONHC₂H₄NHC₃H₆Si(OCH₃)₃ | dark bluish red | 281° C. |
| 2-45 | OCH₃, NH₂, CONH-phenyl | example 1-35 | azo compound with NO₂ and CONH-n-C₁₂H₂₅ | bright red | 327° C. |

TABLE 17

| example No. | amine component | coupler component | structure of azo compound | color | decomposition point |
|---|---|---|---|---|---|
| 2-46 | (OCH₃, NH₂, CONH-phenyl substituted benzene) | example 1-36 | (azo compound structure) | reddish purple | 297° C. |
| 2-47 | (OCH₃, NH₂, CONH-phenyl substituted benzene) | example 1-37 | (azo compound structure) | bluish red | 320° C. |

TABLE 17-continued

| example No. | amine component | coupler component | structure of azo compound | color | decomposition point |
|---|---|---|---|---|---|
| 2-48 | ![amine: 2-methoxy-5-carbamoylphenyl with NH2, OCH3, CONHPh] | example 1-38 | ![azo compound structure with 2-methylnaphthyl-CONH, HO, naphthalene core, CONH-n-C12H25, and azo-linked 2-methoxy-5-(phenylcarbamoyl)phenyl group] | bright red | 329° C. |
| 2-49 | ![amine: 2-methoxy-5-(diethylsulfamoyl)aniline with NH2, OCH3, SO2NEt2] | example 1-11 | ![azo compound structure with 2-methoxy-5-chloro-4-methoxyphenyl-CONH, HO, naphthalene core, CONH-n-C12H25, and azo-linked 2-methoxy-5-(diethylsulfamoyl)phenyl group] | dark purple | 306° C. |

TABLE 18
| example No. | amine component | coupler component | structure of azo compound | color | decomposition point |
|---|---|---|---|---|---|
| 2-50 | 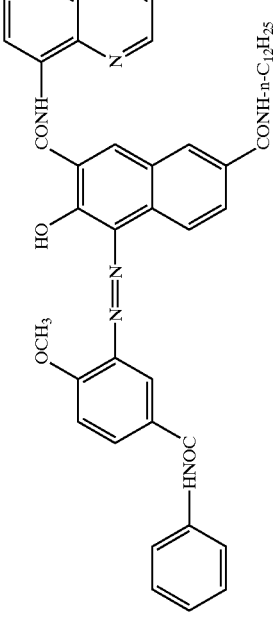 | example 1-39 | | bluish red | 333° C. |
| 2-51 | 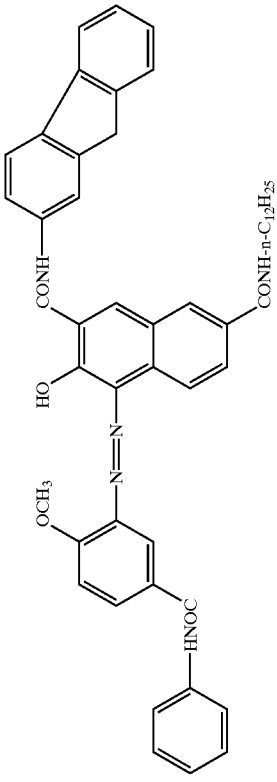 | example 1-40 | | bluish red | 308° C. |

TABLE 18-continued
| example No. | amine component | coupler component | structure of azo compound | color | decomposition point |
|---|---|---|---|---|---|
| 2-52 | 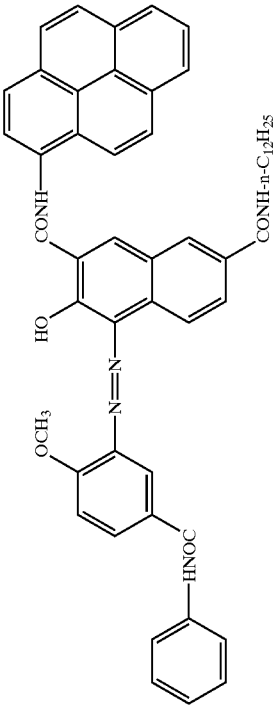 | example 1-41 | | purple | 342° C. |
| 2-53 | 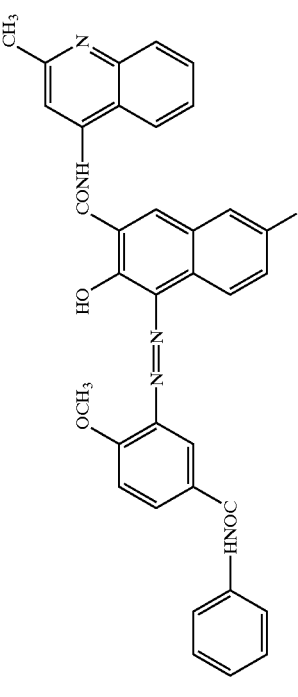 | example 1-42 | | reddish purple | 286° C. |

TABLE 19

| example No. | amine component | coupler component | structure of azo compound | color | decomposition point |
|---|---|---|---|---|---|
| 2-54 | (OCH₃, NH₂, CONH-phenyl substituted benzene) | example 1-43 | azo compound structure | reddish orange | 337° C. |
| 2-55 | (OCH₃, NH₂, CONH-phenyl substituted benzene) | example 1-44 | azo compound structure | dark bluish red | 335° C. |

TABLE 19-continued
| example No. | amine component | coupler component | structure of azo compound | color | decomposition point |
|---|---|---|---|---|---|
| 2-56 |  | example 1-45 |  | bluish red | 333° C. |
| 2-57 |  | example 1-46 |  | bluish red | 325° C. |

TABLE 20

| example No. | amine component | coupler component | structure of azo compound | color | decomposition point |
|---|---|---|---|---|---|
| 2-58 | (OCH₃, NH₂, CONH-phenyl substituted benzene) | example 1-47 | (azo structure) | reddish orange | 309° C. |
| 2-59 | (OCH₃, NH₂, CONH-phenyl substituted benzene) | example 1-48 | (azo structure) | reddish orange | 321° C. |

TABLE 20-continued

| example No. | amine component | coupler component | structure of azo compound | color | decomposition point |
|---|---|---|---|---|---|
| 2-60 | (OCH₃, NH₂, CONH-phenyl) | example 1-49 | (azo compound structure) | bluish red | 335° C. |
| 2-61 | (OCH₃, NH₂, CONH-phenyl) | example 1-50 | (azo compound structure) | reddish orange | 323° C. |

TABLE 21

| example No. | amine component | coupler component | structure of azo compound | color | decomposition point |
|---|---|---|---|---|---|
| 2-62 | (4-methoxy-3-amino-N-phenylbenzamide) | example 1-51 | (azo compound structure) | dark bluish red | 318° C. |
| 2-63 | aniline (C6H5NH2) | example 1-11 | (azo compound structure) | reddish orange | 292° C. |
| 2-64 | 2-methoxy-4-nitroaniline | example 1-11 | (azo compound structure) | reddish purple | 300° C. |
| 2-65 | 4-chloro-2-methylaniline | example 1-11 | (azo compound structure) | bluish red | 322° C. |

TABLE 22

| example No. | amine component | coupler component | structure of azo component | color | decomposition point |
|---|---|---|---|---|---|
| 2-66 | 3-chloroaniline | example 1-11 | azo dye structure with 3-chlorophenyl azo, naphthol, CONH-(2,4-dimethoxy-5-chlorophenyl), and CONH-n-$C_{12}H_{25}$ groups | orange | 289° C. |
| 2-67 | 2-(trifluoromethyl)aniline | example 1-11 | azo dye structure with 2-CF$_3$-phenyl azo, naphthol, CONH-(2,4-dimethoxy-5-chlorophenyl), and CONH-n-$C_{12}H_{25}$ groups | brown | 299° C. |
| 2-68 | 2,5-dichloroaniline | example 1-11 | azo dye structure with 2,5-dichlorophenyl azo, naphthol, CONH-(2,4-dimethoxy-5-chlorophenyl), and CONH-n-$C_{12}H_{25}$ groups | reddish orange | 319° C. |
| 2-69 | 2-methoxy-4-nitroaniline | example 1-46 | azo dye structure with 2-methoxy-4-nitrophenyl azo, naphthol, CONH-(2-methylphenyl), and CONH-n-$C_{12}H_{25}$ groups | reddish brown | 302° C. |

TABLE 23

| example No. | amine component | coupler component | structure of azo compound | color | decomposition point |
|---|---|---|---|---|---|
| 2-70 | 3-chloroaniline | example 1-46 | (azo compound structure with 3-Cl-phenyl-N=N-naphthalene-OH, CONH-o-tolyl, CONH-n-C₁₂H₂₅) | reddish orange | 289° C. |
| 2-71 | 2,5-dichloroaniline | example 1-46 | (azo compound structure with 2,5-diCl-phenyl-N=N-naphthalene-OH, CONH-o-tolyl, CONH-n-C₁₂H₂₅) | orange | 306° C. |
| 2-72 | 2,4,5-trichloroaniline | example 1-46 | (azo compound structure with 2,4,5-triCl-phenyl-N=N-naphthalene-OH, CONH-o-tolyl, CONH-n-C₁₂H₂₅) | reddish orange | 303° C. |
| 2-73 | 2-methoxy-5-(diethylsulfamoyl)aniline | example 1-46 | (azo compound structure with 2-OCH₃-5-Et₂NO₂S-phenyl-N=N-naphthalene-OH, CONH-o-tolyl, CONH-n-C₁₂H₂₅) | yellowish red | 291° C. |

TABLE 24

| example No. | amine component | coupler component |
|---|---|---|
| 2-74 | 2,3-dimethylaniline | example 1-46 |
| 2-75 | 2,4,6-trimethylaniline | example 1-46 |
| 2-76 | 4-amino-2,5-dimethoxy-N-phenylbenzamide | example 1-46 |
| 2-77 | 4-phenoxyaniline | example 1-46 |

| example No. | structure of azo compound | color | decomposition point |
|---|---|---|---|
| 2-74 | (azo compound from 2,3-dimethylaniline coupled with coupler; contains HO, CONH-(2-methylphenyl), and CONH-n-C₁₂H₂₅ groups on naphthalene) | reddish orange | 299° C. |
| 2-75 | (azo compound from 2,4,6-trimethylaniline coupled with coupler; contains HO, CONH-(2-methylphenyl), and CONH-n-C₁₂H₂₅ groups on naphthalene) | yellowish red | 278° C. |

TABLE 24-continued
| 2-76 | 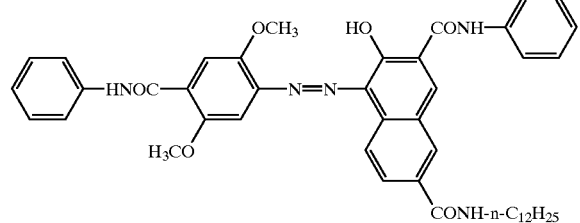 | bluish purple | 304° C. |
|---|---|---|---|
| 2-77 | 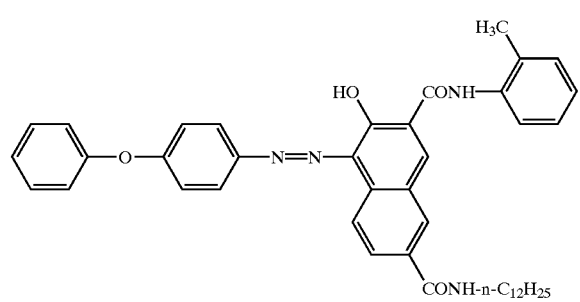 | dark bluish red | 280° C. |

TABLE 25
| example No. | amine component | coupler component | structure of azo compound | color | decomposition point |
|---|---|---|---|---|---|
| 2-78 | 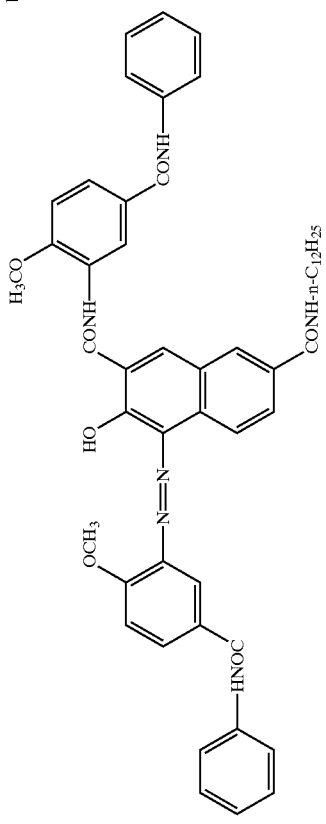 | example 1-52 | | bluish red | 307° C. |
| 2-79 | 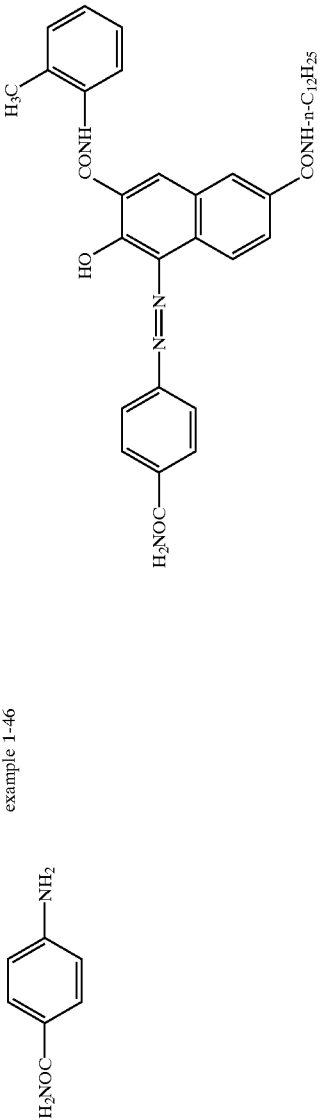 | example 1-46 | | orange | 260° C. |

TABLE 25-continued

| example No. | amine component | coupler component | structure of azo compound | color | decomposition point |
|---|---|---|---|---|---|
| 2-80 | 4-aminobenzamide (H₂NOC–C₆H₄–NH₂) | example 1-50 | (azo compound structure) | reddish orange | 293° C. |
| 2-81 | 2-methoxy-5-methoxyaniline (OCH₃, H₃CO substituted aniline) | example 1-46 | (azo compound structure) | bluish purple | 304° C. |

TABLE 26

| example No. | amine component | coupler component |
|---|---|---|
| 2-82 | 2-ethoxyaniline (OC₂H₅, NH₂) | example 1-46 |
| 2-83 | 4-methoxy-3-amino-N-phenylbenzamide | example 1-53 |
| 2-84 | 4-methoxy-3-amino-N-phenylbenzamide | example 1-54 |
| 2-85 | 2,5-dimethoxy-4-amino-N-phenylbenzamide | example 1-41 |

| example No. | structure of azo compound | color | decomposition point |
|---|---|---|---|
| 2-82 | (azo structure with C₂H₅O, HO, CONH-o-tolyl, CONH-n-C₁₂H₂₅) | yellowish red | 279° C. |
| 2-83 | (azo structure with OCH₃, HNOC-phenyl, HO, CONH-o-tolyl, CONHCH₂CH=CH₂) | bluish red | 308° C. |

TABLE 26-continued

| 2-84 | | yellowish red | 319° C. |

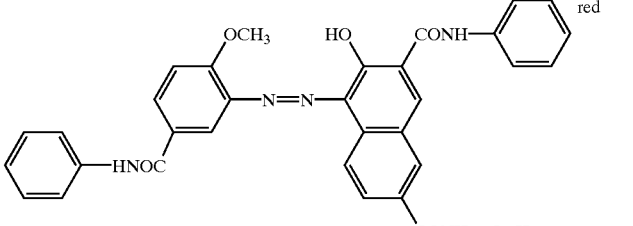

| 2-85 | | purple | 318° C. |

TABLE 27

| example No. | amine component | coupler component | structure of azo compound | color | decomposition point |
|---|---|---|---|---|---|
| 2-86 | 3-fluoroaniline | example 1-46 | | reddish orange | 290° C. |
| 2-87 | 3-fluoroaniline | example 1-50 | | reddish orange | 285° C. |

TEST EXAMPLE 1

Light resistance of the azo compounds obtained in Examples 2-3, 2-5 and 2-6 was evaluated according to the following procedure:

1) 0.4 parts of the sample, and 0.7 parts of dioctylphthalate, 0.7 parts of castor oil were mixed and kneaded by means of Hoover type muller (100 rotation×3).

2) 0.7 parts of the mixture of 1) and 1.3 parts of titanium white were added to 70 parts of the composition consisting of 100 parts of softened polyvinyl chloride, 50 parts of dioctylphthalate, 2 parts of tin maleate, 0.4 parts of calcium stearate and 0.6 parts of barium stearate. The mixture was kneaded by means of twin roll mill at 110° C. for 3 minutes after gelated.

3) 35 parts of the sheet material obtained in 2) was pressed at 100 kgf/cm² to give a flat sheet of 1 mm thick.
4) The flat sheet of 3) was cut into 30 mm×70 mm sample slips.
5) The sample slip, a half of which masked, was irradiated with light by means of feather mater (Shimadzu Seisakusyo; Sun tester XF-180 Xenon lamp). Every 100 hours, the color of the masked and unmasked portion of the sample slip was measured and evaluated the color difference ΔE between them, Evaluation

ΔE<2 A
ΔE=2–3 B
ΔE=3–5 C
ΔE=5–8 D
ΔE>8 E

The color was measured by means of COLOR-EYE 7000 (Gretag Macbeth Co) D65 illuminant, 10 degree of field, reflected light.

The result of the light resistance test regarding the azo compounds obtained in the Examples 2-3, 2-5 and 2-6 are shown in table 28.

TABLE 28

| | structure of azo compound | light resistance test | | | | |
|---|---|---|---|---|---|---|
| | | 100 Hr | 200 Hr | 300 Hr | 400 Hr | 500 Hr |
| 1 | example 2-3 | A | A | A | A | A |
| 2 | example 2-5 | A | A | A | A | A |
| 3 | example 2-6 | A | A | A | A | A |
| comp. ex. 1 | | A | E | — | — | — |

TABLE 28-continued

| | | light resistance test | | | | |
|---|---|---|---|---|---|---|
| | structure of azo compound | 100 Hr | 200 Hr | 300 Hr | 400 Hr | 500 Hr |
| comp. ex. 2* | 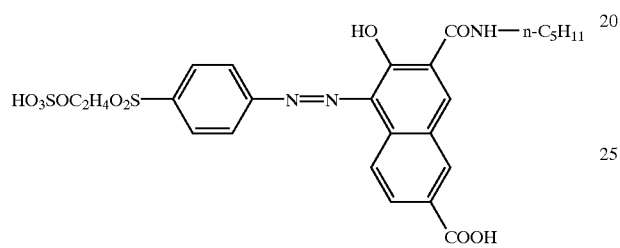 | E | — | — | — | — |

*naphthol red RN (commercially available)

EXAMPLE 3-1

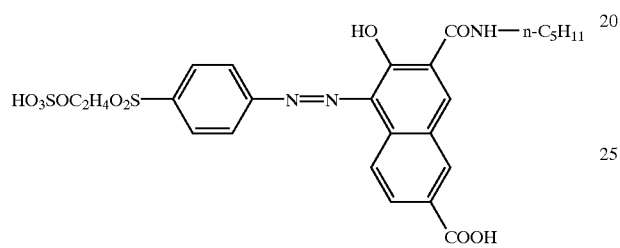

To an ice cooled solution consisting of 2.66 g of 4-(β-sulfate ethylsulfonyl)aniline, which is obtained by a known method, 6.6 g of $H_2SO_4$ and 150 g of water, 1.04 g of sodium nitrite in 10 g of water was added dropwise to conduct diazotizing reaction.

Thus obtained diazonium compound was added dropwise to the coupler solution consisting of 30 g of water, 60 g of 10% aqueous NaOH, 40 g of N-methyl-2-pyrrolidone and 2.94 g of 2-hydroxy-6-hydroxycarbonyl-3-n-pentylamino carbonyl naphthalene over 30 minutes at 0–5° C. to conduct coupling reaction in a conventional manner. The mixture was stirred for few hours at 15° C. until the reaction was completed. During the reaction, pH of the reaction mixture was kept within the range of 4–6 by means of 10% aqueous $NaHCO_3$. After the reaction, the mixture was subjected to salting-out with sodium chloride and filtration to isolate 5.28 g of red powdery crystal containing sodium chloride.

This compound exhibits good properties as a reactive dye. A cellulose fiber material, such as cotton fiber, was dyed with the compound in a conventional manner to provide a brownish orange color with good chloride resistance, light resistance, alkaline perspiration resistance, and rub resistance.

Figure 3:
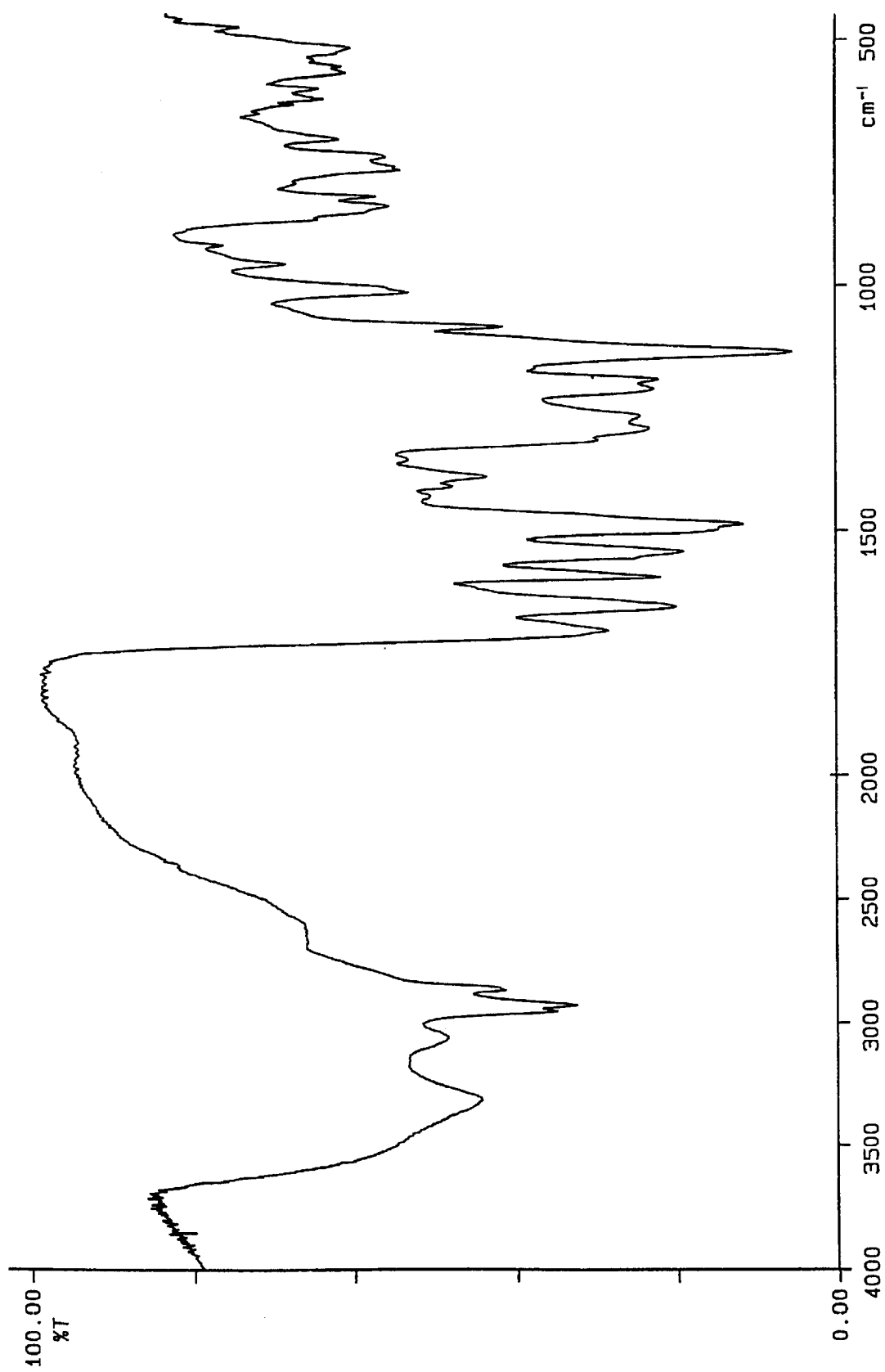
FIG. 3 shows an infrared absorption spectrum of the compound obtained in Example 3-1.

The infrared spectrum (by KBr method) of the composition is shown in FIG. 3 (λmax=471.5 nm).

EXAMPLE 3-2

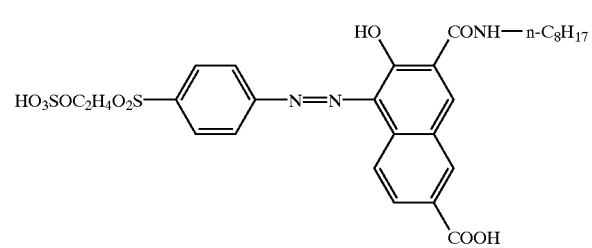

According to the same manner as described in Example 3-1 with the exception that 3.36 g of 2-hydroxy-6-hydroxycarbonyl-3-n-octylaminocarbonyl naphthalene was used instead of 2-hydroxy-6-hydroxycarbonyl-3-n-pentylaminocarbonyl naphthalene, and the amount of 10% aqueous NaOH and N-methyl-2-pyrrolidone in the coupler solution were changed to 20 g and 3 g respectively, 4.79 g of red powdery crystal containing sodium chloride was obtained.

This compound exhibits good properties as a reactive dye. A cellulose fiber material, such as cotton fiber, was dyed with the compound in a conventional manner to provide a brownish orange color with good chloride resistance, light resistance, alkaline perspiration resistance, and rub resistance.

Figure 4:
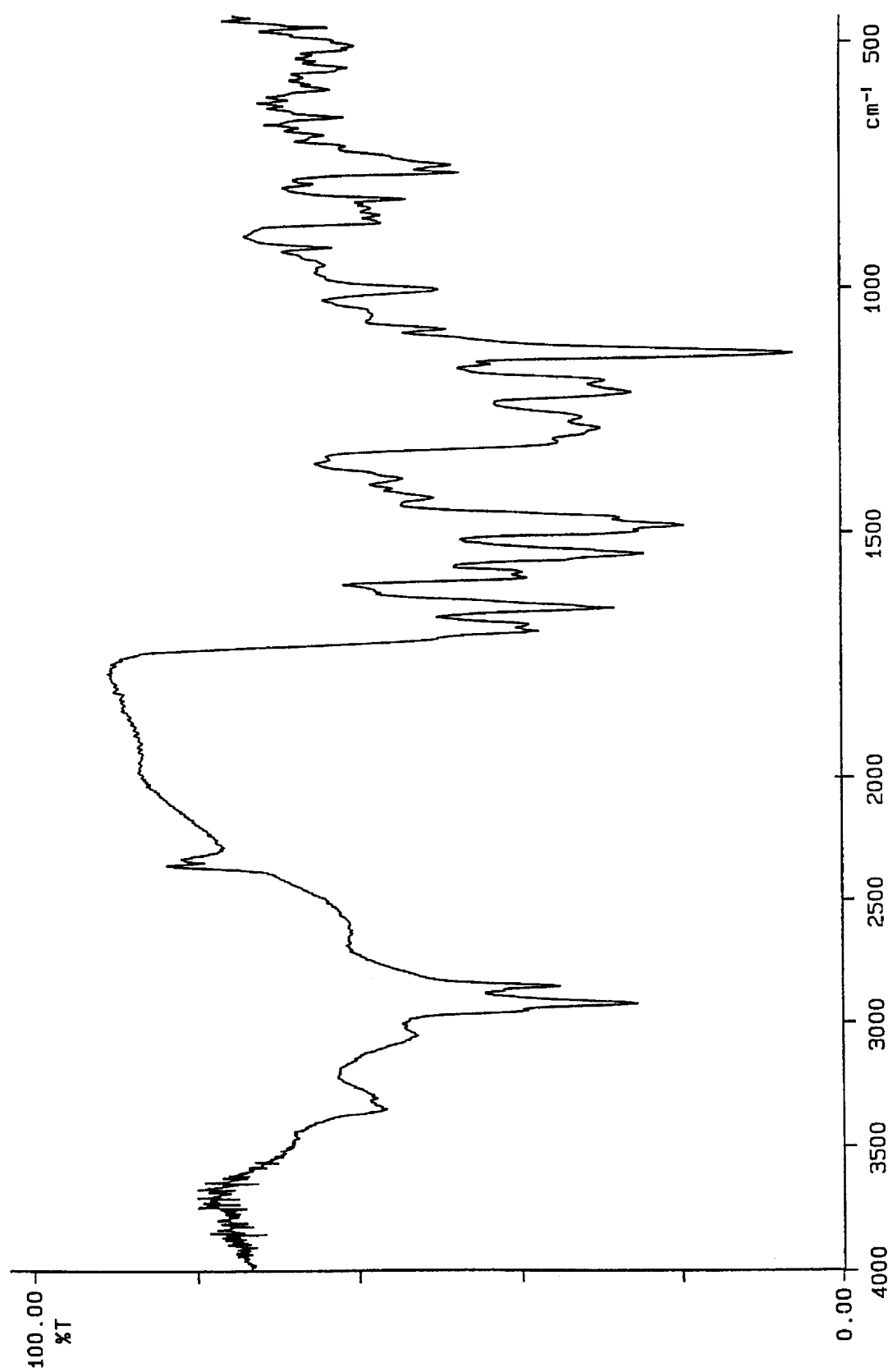
FIG. 4 shows an infrared absorption spectrum of the compound obtained in Example 3-2.

The infrared spectrum (by KBr method) of the composition is shown in FIG. 4 (λmax=479.0 nm).

EXAMPLE 3-3

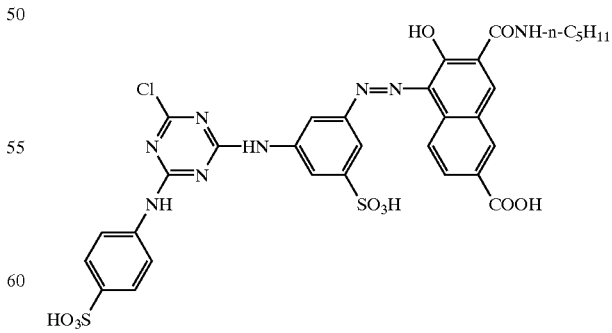

a) Sulfanilic acid (18.2 g) was added to about 100 g of water and the pH was adjusted to about 6 by means of 10% aqueous $NaHCO_3$ to dissolve the sulfanilic acid. The solution was poured into dispersion of 20 g of cyanyl chloride in 160 g of ice-cold water and stirred at 0–5° C. in an ice bath until sulfanilic acid disappeared. During the reaction, the pH was kept within the range of 3.5–4.5 by means of 10% aqueous NaHCO$_3$.

b) m-phenylenediamine-4-sulfonate (1 8.8 g) was added to about 10 g of water, the pH was adjusted to 6–7 by means of 10% aqueous NaHCO$_3$ to dissolve m-phenylenediamine-4-sulfonate. Into the solution, the reactant obtained in a) was poured and warmed to 40° C. and stirred until m-phenylenediamine-4-sulfonate disappeared. During this reaction, the pH of the reaction mixture was kept in the range of 5–6 by means of 10% aqueous NaHCO$_3$.

c) 26.6 g of 35% aqueous HCl and 200 g of water was added to the condensate solution obtained in b), and then, 7 g of aqueous sodium nitrite was added dropwise in an ice bath to conduct diazotization. Resulting diazonium solution was added dropwise to the coupler solution consisting of 31.2 g of 2-hydroxy-6-hydroxycarbonyl-3-n-pentylamino carbonyl naphthalene and 80.0 g of 10% aqueous NaOH in 600 g of 50% aqueous 1-methyl-2-pyrrolidone, and conducted coupling reaction in a conventional manner. The reaction mixture was stirred for a several hours until the coupling reaction was completed. The obtained mixture was subjected to salting-out and filtration to isolate 123.7 g of red powdery crystal containing sodium chloride.

This compound exhibits good properties as a reactive dye. A cellulose fiber material, such as cotton fiber, was dyed with the compound in a conventional manner to provide a yellowish orange color with good chloride resistance, light resistance, alkaline perspiration resistance, and rub resistance.

Figure 5:
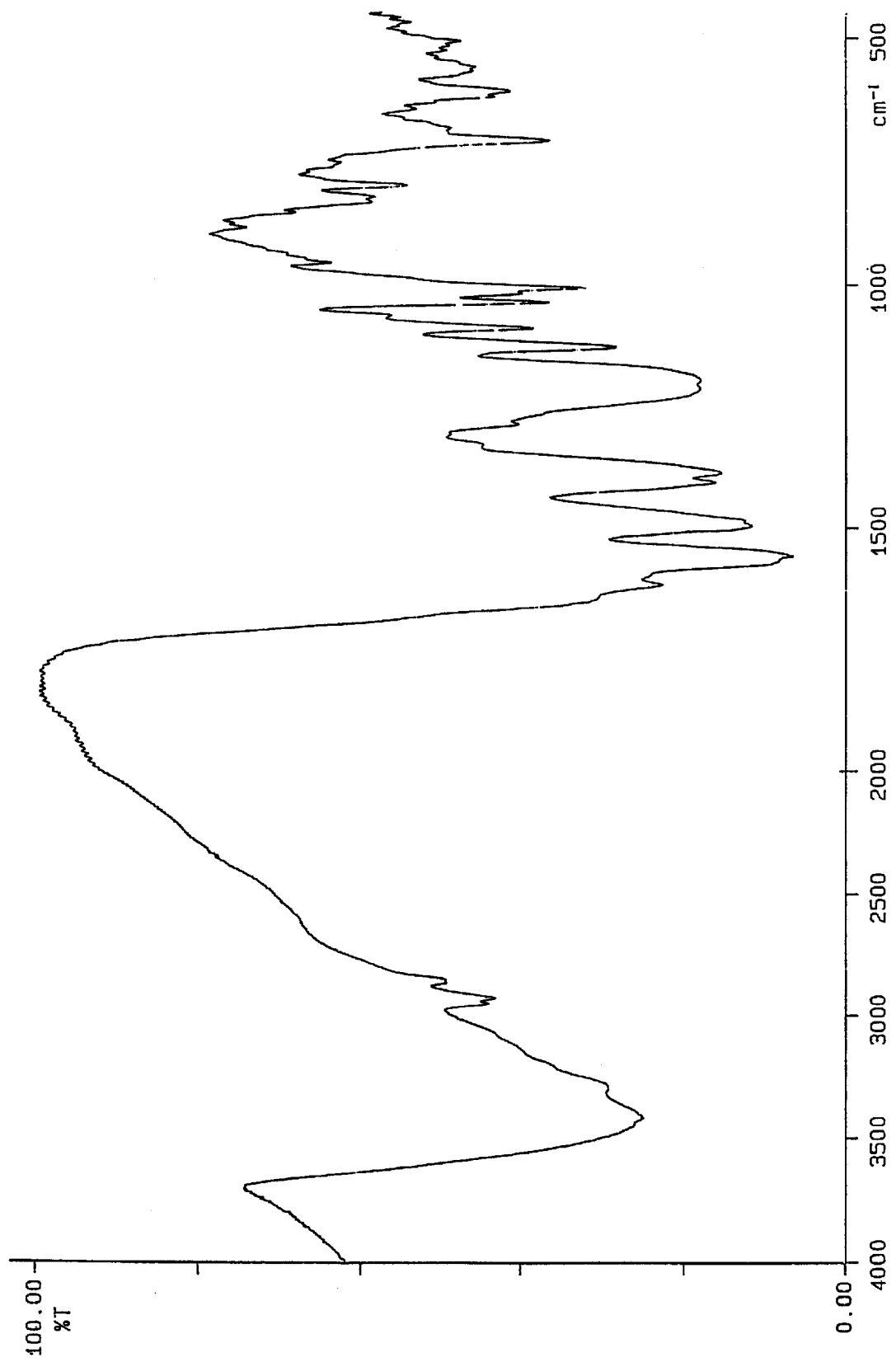
FIG. 5 shows an infrared absorption spectrum of the compound obtained in Example 3-3.

The infrared spectrum (by KBr method) of the composition is shown in FIG. 5 (λmax=502.5 nm).

EXAMPLE 3-4

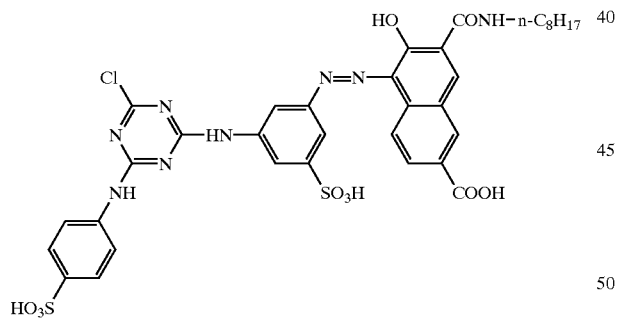

According to the same manner as described in Example 3-3 with the exception that, 34.4 g of 2-hydroxy-6-hydroxycarbonyl-3-n-octylaminocarbonyl naphthalene was used in the step c) instead of 2-hydroxy-6-hydroxycarbonyl-3-n-pentylaminocarbonyl naphthalene, and the amount of 50% aqueous 1-methyl-2-pyrrolidone in the coupler solution were changed to 5009, 71.8 g of red powdery crystal containing sodium chloride was obtained.

This compound exhibits good properties as a reactive dye. A cellulose fiber material, such as cotton fiber, was dyed with the compound in a conventional manner to provide a yellowish orange color with good chloride resistance, light resistance, alkaline perspiration resistance, and rub resistance.

Figure 6:
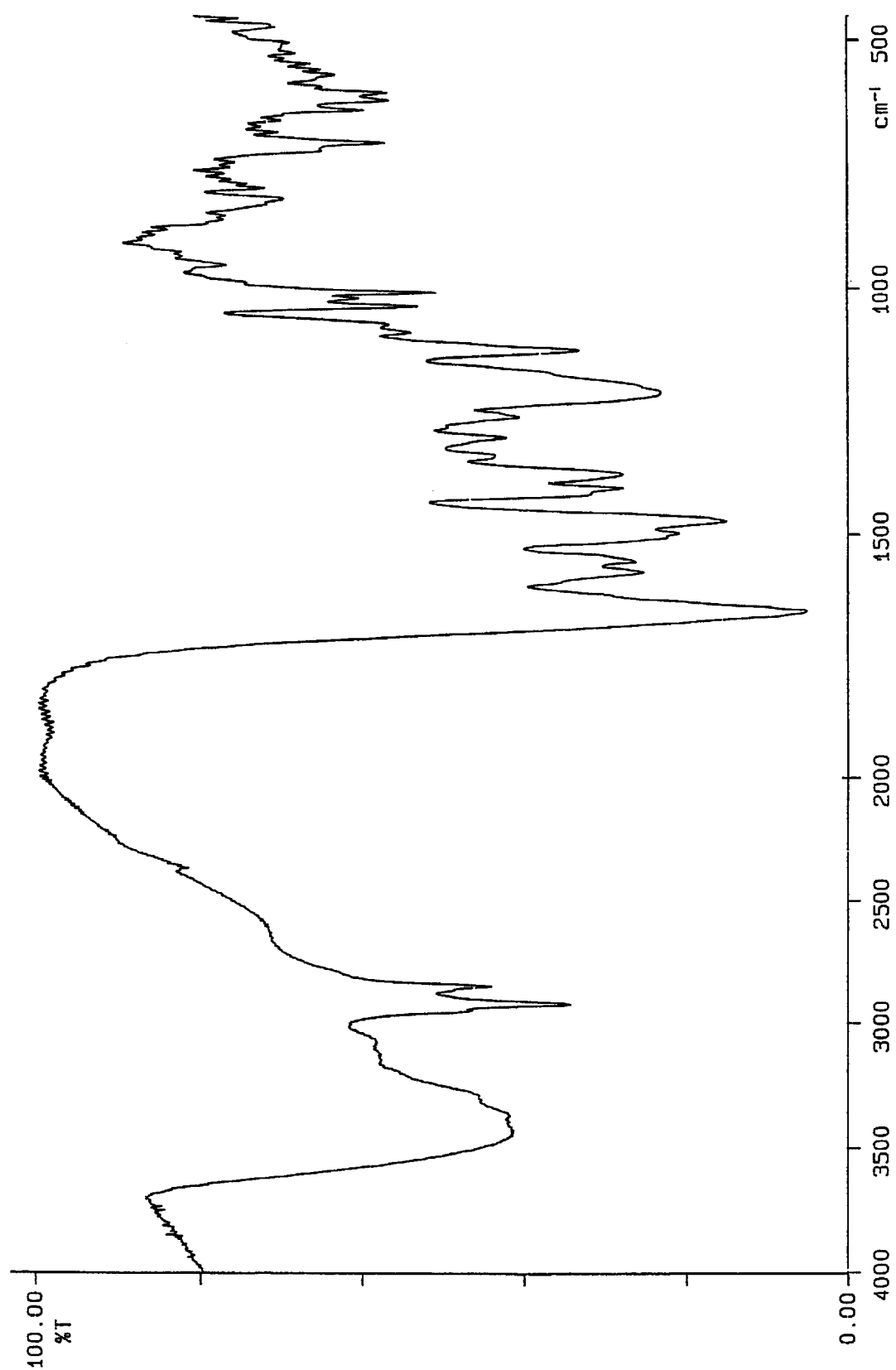
FIG. 6 shows an infrared absorption spectrum of the compound obtained in Example 3-4.

The infrared spectrum (by KBr method) of the composition is shown in FIG. 6 (λmax=498.5 nm).

Industrial Applicability

The monoazo compositions synthesized with the novel naphthol derivatives of the present invention are novel and exhibit good fastness with excellent water resistance, chemical resistance, solvent resistance, thearmal resistance, and especially light resistance. and also good dispersibility and coloring power. The pigments comprising the azo compounds of the present invention can provide a wide range of color and good transparency.

What is claimed is:

1. An azo compound having the general formula [I]:

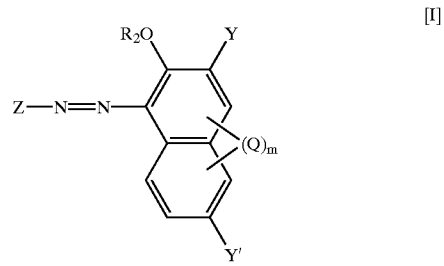

wherein Y is —(CONH)n-X or an optionally esterified carboxyl group,

Y' is —(CONH)n-X' or an optionally esterified carboxyl group, (wherein X and X' are optionally substituted and/or branched saturated or unsaturated aliphatic hydrocarbon groups, optionally substituted aromatic groups, or optionally substituted heterocyclic groups having conjugated double bonds, n is an integer of 1 or 2, provided that when either Y or Y' is a carboxylic group, said carboxylic group may optionally form an acceptable salt), R$_2$ is a hydrogen atom, an optionally branched alkyl group having 1–6 carbon atoms, an acyl group having 1–6 carbon atoms or a phenyl alkyl group, Q is an optionally branched alkyl group having 1–6 carbon atoms, an optionally branched alkoxy group having 1–6 carbon atoms, a halogen atom, a sulfo group, a nitro group, a nitroso group, or an amino group, m is an integer of 0–3, provided that when m is 1, the Q may be combined with either of the two condensed rings, when m is 2 or 3, the Qs may be combined with either or both of the condensed rings, or may form a ring together with the two condensed rings, and Z is an optionally substituted monovalent aromatic group; provided that at least one of Y and Y' represents a group wherein X or X' is an optionally substituted and/or branched unsaturated or saturated aliphatic hydrocarbon group.

2. The azo compound of claim 1, wherein Y is —(CONH)n-X and Y' is —(CONH)n-X' (wherein n, X and X' are the same as above), and one of X and X' is an optionally substituted and/or branched saturated or unsaturated aliphatic hydrocarbon group.

3. The azo compound of claim 2, wherein one of X and X' is an optionally substituted and/or branched saturated or unsaturated aliphatic hydrocarbon group having 1–20 carbon atoms and the other is an optionally substituted naphthyl group.

4. The azo compound of claim 1, wherein Z is an optionally substituted phenyl or naphthyl group.

5. An azo pigment comprising the azo compound of claim 1.

6. An ink composition comprising the azo compound of claim 1.

7. A paint composition comprising the azo compound of claim 1.

8. A dye composition comprising the azo compound of claim 1.

9. A mass coloring agent for a polymer material comprising the azo compound of claim 1.

10. A process for preparing the azo compound of the claim 1, comprising the steps of diazotizing an aromatic amine having the formula [II]

Z—NH$_2$     [II]

wherein Z is an optionally substituted aromatic group, and coupling thus obtained diazonium compound with a compound having the general formula [III]:

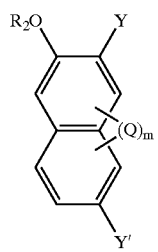

[III]

wherein Y is —(CONH)n-X or an optionally esterified carboxyl group,

Y' is —(CONH)n-X' or an optionally esterified carboxyl group, (wherein X and X' are optionally substituted and/or branched saturated or unsaturated aliphatic hydrocarbon groups, optionally substituted aromatic groups, or optionally substituted heterocyclic groups having conjugated double bonds, n is an integer of 1 or 2, provided that when either Y or Y' is a carboxylic group, said carboxylic group may optionally form an acceptable salt), R$_2$ is a hydrogen atom, an optionally branched alkyl group having 1–6 carbon atoms, an acyl group having 1–6 carbon atoms or a phenyl alkyl group, Q is an optionally branched alkyl group having 1–6 carbon atoms, an optionally branched alkoxy group having 1–6 carbon atoms, a halogen atom, a sulfo group, a nitro group, a nitroso group, or an amino group, and m is an integer of 0–3, provided that when m is 1, the Q may be combined with either of the two condensed rings, when m is 2 or 3, the Qs may be combined with either or both of the condensed rings, or may form a ring together with the two condensed rings;

provided that at least one of Y and Y' represents a group wherein X or X' is an optionally substituted and/or branched unsaturated or saturated aliphatic hydrocarbon group;

provided that when either Y or Y' is a carboxylic group, said group may form a lake compound together with an appropriate metal salt.

11. A naphthol derivative having the general formula (IV):

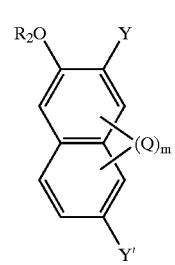

[IV]

wherein Y is —(CONH)n-X or an optionally esterified carboxyl group,

Y' is —(CONH)n-X' or an optionally esterified carboxyl group, (wherein X and X' are optionally substituted and/or branched saturated or unsaturated aliphatic hydrocarbon groups, optionally substituted aromatic groups, or optionally substituted heterocyclic groups having conjugated double bonds, n is an integer of 1 or 2, provided that when either Y or Y' is a carboxylic group, said carboxylic group may optionally form an acceptable salt), R$_2$ is a hydrogen atom, an optionally branched alkyl group having 1–6 carbon atoms, an acyl group having 1–6 carbon atoms or a phenyl alkyl group, Q is an optionally branched alkyl group having 1–6 carbon atoms, an optionally branched alkoxy group having 1–6 carbon atoms, a halogen atom, a sulfo group, a nitro group, a nitroso group, or an amino group, m is an integer of 0–3, provided that when m is 1, the Q may be combined with either of the two condensed rings, when m is 2 or 3, the Qs may be combined with either or both of the condensed rings, or may form a ring together with the two condensed rings, and provided that at least one of Y and Y' represents a group wherein X or X' is an optionally substituted and/or branched unsaturated or saturated aliphatic hydrocarbon group.

12. An ink composition for ink-jet printing system, comprising the pigment of the claim 5.

13. A toner composition for electrophotographic system, comprising the pigment of the claim 5.

14. A color filter, comprising the pigment of the claim 5.

15. An organic photosensitive member, comprising the pigment of the claim 5.

* * * * *